US012773419B2

(12) United States Patent
Sinha et al.

(10) Patent No.: US 12,773,419 B2
(45) Date of Patent: Oct. 27, 2026

(54) PHARMACOLOGICAL AGENTS FOR TREATING CONDITIONS OF THE EYE

(71) Applicant: PLEX PHARMACEUTICALS, INC., San Diego, CA (US)

(72) Inventors: Santosh C. Sinha, San Diego, CA (US); Sridhar Govinda Prasad, San Diego, CA (US); Marshall C. Peterman, San Diego, CA (US)

(73) Assignee: PLEX PHARMACEUTICALS, INC., San Diego, CA (US)

(*) Notice: Subject to any disclaimer, the term of this patent is extended or adjusted under 35 U.S.C. 154(b) by 482 days.

(21) Appl. No.: 18/037,021

(22) PCT Filed: Nov. 15, 2021

(86) PCT No.: PCT/US2021/072405
§ 371 (c)(1),
(2) Date: May 15, 2023

(87) PCT Pub. No.: WO2022/104383
PCT Pub. Date: May 19, 2022

(65) Prior Publication Data

US 2024/0000812 A1 Jan. 4, 2024

Related U.S. Application Data

(60) Provisional application No. 63/215,818, filed on Jun. 28, 2021, provisional application No. 63/113,691, filed on Nov. 13, 2020.

(51) Int. Cl.

| | |
|---|---|
| ***A61K 31/662*** | (2006.01) |
| ***A61K 31/198*** | (2006.01) |
| ***A61K 31/46*** | (2006.01) |
| ***A61K 31/661*** | (2006.01) |
| ***A61P 27/10*** | (2006.01) |
| ***C07F 9/12*** | (2006.01) |
| ***C07F 9/38*** | (2006.01) |

(52) U.S. Cl.
CPC .......... *A61K 31/662* (2013.01); *A61K 31/198* (2013.01); *A61K 31/46* (2013.01); *A61K 31/661* (2013.01); *A61P 27/10* (2018.01); *C07F 9/12* (2013.01); *C07F 9/3808* (2013.01)

(58) Field of Classification Search
CPC .............................. A61P 27/10; A61K 31/662
See application file for complete search history.

(56) References Cited

U.S. PATENT DOCUMENTS

| | | | |
|---|---|---|---|
| 8,524,758 B2 | 9/2013 | Benozzi | |
| 2004/0002461 A1 | 1/2004 | Matier et al. | |
| 2014/0296188 A1* | 10/2014 | Centellas Casado | ... A61P 25/28 514/567 |
| 2015/0274633 A2 | 10/2015 | Ducki et al. | |
| 2019/0183842 A1 | 6/2019 | Huang et al. | |
| 2020/0234607 A1* | 7/2020 | Keita | ..................... G02C 7/027 |

FOREIGN PATENT DOCUMENTS

| | | | |
|---|---|---|---|
| WO | 2014164667 | A1 | 10/2014 |
| WO | 2015/095257 | A2 | 6/2015 |
| WO | 2019/195761 | A2 | 10/2019 |
| WO | WO 2019/195761 | * | 10/2019 |
| WO | 2022/257986 | A1 | 12/2022 |
| WO | 2023/278464 | A1 | 1/2023 |

OTHER PUBLICATIONS

Extended European Search Report and Search Opinion received for European Application No. 21893092.3, mailed on Jul. 24, 2024, 12 pages.
Junfeng et al., "Levodopa Inhibits the Development of Form-Deprivation Myopia in Guinea Pigs", Optometry and Vision Science, Published For the Academy by Williams & Wilkins, vol. 87, No. 1, Jan. 1, 2010, 8 pages.
Kiss et al., "Discovery of a long-acting, peripherally selective inhibitor of Catechol-O-Methyltransferase", Journal of medicinal Chemistry, American Chemical Society, US, vol. 53, No. 8, Apr. 22, 2010, pp. 3396-3411.
Landis et al., "Increased endogenous dopamine prevents myopia in mice", Experimental Eye Research, Academic Press Ltd, London, vol. 193, 107956, Feb. 4, 2020, 9 pages.
Nelson et al., "Blinded potency comparison of transthyretin kinetic stabilisers by subunit exchange in human plasma", Amyloid, vol. 28, No. 1, Aug. 18, 2020, 7 pages.
Unknown, "2377757-97-4, 2377757-96-3, 923287-50-7, 747401-28-1", STN, 2019, pp. 1-6.
Singh S et al. "Ocular Manifestations of Emerging Flaviviruses and the Blood-Retinal Barrier", vol. 10, No. 10, Sep. 28, 2018. pp. 1-20.
Mathebula SD, Makunyane PS, "Loss of amplitude of accommodation in pre-presbyopic HIV and AIDS patients under treatment with antiretrovirals", African Vision and Eye Health, 2017; 76 (1), a411. https://doi.org/10.4102/aveh.v76i1.411 pp. 1-6.
Westcott MC et al., "Failure of accommodation in patients with HIV infection", vol. 15, Pt. 4, Aug. 2001, p. 474-478.
International Search Report and Written Opinion mailed on Apr. 5, 2022 in PCT/US2021/072405.

* cited by examiner

*Primary Examiner* — Marcos L Sznaidman
(74) *Attorney, Agent, or Firm* — ArentFox Schiff LLP

(57) ABSTRACT

Provided are compounds useful for treating, preventing, reducing the occurrence of, slowing the progression of, or reducing, ameliorating, or alleviating the symptoms associated with a condition selected from the group consisting of: presbyopia, cataract, transthyretin (TTR)-associated amyloidosis, myopia, or other conditions or disorders associated with the eye, including COMT inhibitors and pro-drugs thereof, and methods of using these compounds.

6 Claims, 4 Drawing Sheets

PHARMACOLOGICAL AGENTS FOR TREATING CONDITIONS OF THE EYE

CROSS-REFERENCE TO RELATED APPLICATIONS

This application is a National Stage Entry of PCT/US2021/072405, filed Nov. 15, 2021, which claims priority to U.S. Provisional Patent Application No. 63/113,691, filed Nov. 13, 2020, and U.S. Provisional Patent Application No. 63/215,818, filed Jun. 28, 2021, each of which are incorporated by reference in their entirety.

BACKGROUND

Myopia, or short-sightedness, is a refractive disorder arising from a mismatch between the optical power of the eye and its axial length. This mismatch is a result of excessive elongation of the eye during development and into young adulthood, which leads to the focal plane of distant objects falling in front of the retina, instead on it, causing the image to appear blurred. Myopia is now recognized as a leading cause of visual impairment and low vision worldwide (Holden, B. A. et al. 2015). Over the past 50 years, myopia rates have increased dramatically, with some estimates predicting that half of the world's population could be affected by short-sightedness by 2050. The rapid rise in myopia prevalence is most evident in educationally developed areas of East and Southeast Asia (Morgan, I. G. et al., 2012).

The increase in the prevalence of myopia pose two main challenges. The first challenge is the need to provide optical or other corrections for the associated refractive error for a large percentage of the population. The second, and arguably an even greater challenge comes from the increased prevalence of high myopia, and its associated sight-threatening pathological changes (Morgan, I. G. et al., 2017). Correction of refractive error does not prevent the development of these pathological changes, the chances of which increase with the severity of myopia, as it does not address the excessive elongation of the eye. Such pathologies include chorioretinal changes including retinal detachments, myopic macular degeneration, and staphyloma, as well as an increased risk of other sight-threatening conditions such as glaucoma and cataracts (Ohno-Matsui, K., 2017). The US National Eye Institute has estimated the annual cost for treating refractive disorders in the US alone at just under $14 billion in 2010 and rising (Rein, D. B., 2013), not including considerable indirect costs such as lost productivity.

Myopia and high myopia were estimated to affect 27% (1893 million) and 2.8% (170 million) of the world population, respectively, in 2010. According to published studies, the prevalence of myopia is highest in east Asia, where China, Japan, the Republic of Korea and Singapore have a prevalence of approximately 50%, and lower in Australia, Europe, and north and south America (Holden B et al., 2016). Myopic macular degeneration (MMD) is the most common cause of visual impairment in patients with myopia, as 10% of people with pathologic myopia develop MMD (due to choroidal neovascularization), which is bilateral in 30% of cases (Ohno-Matsui K et al., 2003).

Animal studies have demonstrated that ocular growth is regulated locally in response to visual stimuli by pathways originating in the retina, with the retinal transmitter dopamine playing a key role (Feldkaemper, M. & Schaeffel, F., 2004). Dopamine release is strongly affected by light and the spatiotemporal properties of visual inputs, with dysregulation of the dopaminergic system heavily implicated in the development of experimental myopia. Specifically, in multiple species, retinal dopamine synthesis and release has been shown to be significantly down-regulated during the development of experimental myopia (Iuvone, P. M. et al., 1989; Bergen, M. A. et al., 2016), whilst pharmacological administration of dopamine agonists which mimic the effects of dopamine have been shown to inhibit the development of experimental myopia (Feldkaemper, M. & Schaeffel, F., 2013). Furthermore, intravitreal administration of exogenous dopamine in rabbits and systemic administration of its precursor levodopa (L-DOPA) in guinea pigs inhibit the development of experimental myopia, while retina-specific tyrosine hydroxylase knockout mice and mice treated with 6-hydroxydopamine, which depletes the retina of dopaminergic neurons, show a myopic shift in refraction (Wu, X. H. et al., 2016). Finally, dopaminergic activity appears to underlie the mechanism by which bright light exposure, or exposure to brief periods of normal vision, prevents the development of experimental myopia, specifically form-deprivation myopia (FDM), in the chick (McCarthy, C. S. et al., 2007).

The potential role of dopamine in the regulation of ocular growth, combined with the significant down regulation of retinal dopamine synthesis and release observed in multiple species during the development of experimental myopia, suggests that preserving and/or increasing dopamine levels could potentially prevent ocular growth and therefore prevent the development of myopia. In support of these studies, intravitreal administration of L-Dopa, which is converted into dopamine has been shown to inhibit the development of experimental myopia in chickens (Kate Thomson, et al., 2019). Unfortunately, administration of L-Dopa is accompanied with several side effects. L-Dopa and some of its metabolites have been shown to have pro-oxidant properties, and oxidative stress has been shown to increase the pathogenesis of Parkinson's disease (Mao J, et al., 2010). Promotion of free-radical formation by L-Dopa seems to directly affect its potential as a treatment for myopia due to the fact that free-radicals could cause further damage to proteins that are responsible for controlling structural proteins in the eye. It has also been shown that L-Dopa and some of its metabolites such as dopa/dopamine and quinone are toxic for nigral neurons. The toxic effect of L-Dopa limits its use for the treatment of myopia.

Cataracts are the leading cause of blindness (51%) worldwide according to the World Health Organization (WHO), particularly in low- and middle-income countries. Data dating back to the beginning of this millennium showed that 30-60% of blindness in Africa and 60-80% in South-East Asia is attributable to cataracts. In the United States, the current number of those with cataract is estimated to be more than 25.7 million. Projections from Prevent Blindness research estimate that the number will increase to 38.5 million by 2032, and to 45.6 million by the year 2050. Cataract is a clouding of the eye's lens which blocks or changes the passage of light into the eye. Cataracts usually form in both eyes, but not at the same rate. They can develop slowly or quickly, or progress to a certain point, then not get any worse. Besides aging, other factors may cause cataracts to form. Eye infections, some medicines (such as steroids), smoking, injuries, trauma, or exposure to intense heat or radiation may cause cataracts. Too much exposure to non-visible sunlight (called UV or ultraviolet light) and various diseases, such as diabetes or metabolic disorders, may also contribute to cataracts formation.

The only treatment currently available is surgical extraction of the lens and replacement with an interocular lens that is accompanied by a high public health burden. Although cataract surgery is generally considered to be safe, there are significant complications: (i) 30-50% of patients in the US having cataract surgery develop opacification of the posterior lens capsule within two years and require laser treatment; (ii) 0.8% have retinal detachments; (iii) 0.6-1.3% are hospitalized for corneal edema or require corneal transplantation and (iv) about 1% are presented with endophthalmitis. In addition, in many remote and poor areas of the developing and under-developed regions of the world, people still remain blind from cataract, primarily due to lack of access to eye care.

Presbyopia is the loss of accommodative ability of the eye resulting in the inability to focus on near objects. Presbyopia affects everyone over the age of 45 and has significant negative impacts on the quality of life. Current treatments for presbyopia include: (i) non-invasive approaches that utilize devices to help improve near and distance vision but do nothing to restore the natural process of accommodation and require constant use of the devices, and (ii) invasive surgical procedures which are associated with major complications including decrease in vision quality, regression effects, anisometropia, corneal ectasia, and haze. Most importantly, none of these methods can reverse presbyopia. Moreover, no treatment option exists that can either prevent or delay the onset of presbyopia.

Stiffening of eye lens and changes in the elasticity of the lens capsule, dimension of eye lens, dimension of the zonular attachment, and ciliary muscle (CM) contractions, have all been proposed as contributing factors for presbyopia. However, human and non-human primate studies suggest that CM function is normal well beyond the onset of presbyopia. By contrast, the human lens increases in stiffness with age in a manner that directly correlates with a loss in accommodative power. The loss in accommodative power can be restored by implanting intraocular lenses made from a flexible polymer suggesting that restoration of lens flexibility is sufficient to restore accommodation. Therefore, a pharmacological agent that could prevent or reverse the hardening of the crystalline lens would provide a promising avenue for a novel non-invasive treatment for presbyopia.

At the molecular level, proteins known as crystallins play a major role in the opacification and stiffening of the eye lens. The lens crystallins comprise three isoforms, α, β, and γ and make up 90% of the eye lens protein content. α crystalline (AC), an ATP-independent chaperone and member of the small heat shock protein (sHsp) family, constitutes 40% of the crystallin protein content. It exists as a hetero-oligomer of two subunits, αA-crystallin (AAC) and αB-crystallin (ABC) and its expression is primarily restricted to the eye lens. It recognizes exposed conformational features in partially unfolded lens proteins and sequesters them from one another, thereby reducing the population of aggregation-prone species that would otherwise lead to various age-related vision impairment.

Multiple studies have established a link between stiffening of the human lens and AC function. Dynamic mechanical analysis measurements have shown that there is a significant increase in the stiffness of the lens with age, particularly in the lens nucleus where a 500- to 1000-fold decrease in elasticity is observed. This increase in lens stiffness correlates with the age-related decline in free AC chaperone concentration as most AC becomes incorporated into high molecular weight (HMW) aggregates by the age of 40-50. This conversion of soluble AC into HMW aggregates is accompanied by a large increase in lens stiffness, presumably because the low level of soluble AC present is not sufficient to chaperone denatured proteins. That age-related decrease in free AC chaperone is responsible for lens stiffness is supported by experiments where human lenses were subjected to heating to mimic the age-related conversion of soluble AC into HMW aggregates and an increase in lens stiffness was observed. Similarly, purified soluble AC forms HMW aggregates when exposed to UV radiation with a loss in chaperone like activity. The HMW aggregate is formed due to the intermolecular cross-linking, particularly S—S bonds, resulting from the oxidation of cysteine sulfhydryl groups (—SH). The formation of this disulfide cross-linked HMW aggregate is thought to be a major contributor in increasing the stiffness and loss of accommodation amplitude of the lens.

It has been suggested that presbyopia is the earliest observable symptom of age-related nuclear (ARN) cataract, a major cause of blindness in the world.

Given the need for noninvasive treatment that can protect and restore the accommodative ability of the eye lost in presbyopia and given that formation of HMW AC aggregates is a major causative factor underlying presbyopia and cataracts, there is a need for the development of pharmacological agents that can selectively delay and/or reverse the HMW AC aggregate formation. To overcome the adverse side effect of L-Dopa when used as a treatment for myopia, the present disclosure provides an alternate approach, which is to prevent the breakdown of endogenous dopamine by inhibiting the enzymes responsible for its metabolism using safe and effective small molecule inhibitors that can be delivered topically to the retina. Two enzymes are known to be involved in the metabolic inactivation of dopamine, namely Catechol-O-methyl transferase (COMT) and Monoamine oxidase (MAO) (FIG. 1) (Axelrod, J., and Tomchick, R., 1958; Tosini, G and Iuvone, P. M., 2014).

COMT catalyzes the O-methylation of catecholamines with S-adenosyl methionine as a methyl donor. The role of these enzymes in the inactivation of dopamine is well-accepted. MAO oxidatively deaminates amines. Given that these two enzymes are expressed in the ocular tissues of albino rabbits (Waltman, S and M Sears, 1964), combined with the observation that COMT RNA expression has been detected in human retina (https://www.proteinatlas.org/ENSG00000093010-COMT/tissue), inhibiting either one or both of these enzymes may be helpful for treating of myopia.

Several safe and potent inhibitors of COMT are known. These include Nitecapone ($IC_{50}$ 300 nm, MW 265.2 Da), Entacapone ($IC_{50}$ 151 nm, MW 305.3 Da), Tolcapone ($IC_{50}$ 773 nm, MW 273.2 Da), Nebicapone ($IC_{50}$ 3.7 nm, MW 273.2 Da), Opicapone (Ki 1 nm, MW 413.2 Da), BIA 3-335 (Ki 6 nm, MW 439.4 Da), and Bifunctional inhibitor ($IC_{50}$ 300 nm, MW 346.3 Da). Where, IC 50 is the concentration of the inhibitor that affords a 50% inhibition in the activity of the enzyme, COMT.

Provided herein is a rational structure activity relation-based approach for identifying small molecule disaggregases (SMDs) that can inhibit the formation and/or dissolve HMW aggregates of human ACC (hAAC). Several SMDs were identified based on this approach. It is believed that these SMDs are useful for the treatment and management of presbyopia, and for the treatment and/or slowing down the progression of cataract. The cataract can be age-related (nuclear sclerotic, cortical, and posterior subcapsular), congenital, familial, secondary, traumatic, smoke-related and radiation cataracts.

All references discussed herein are incorporated by reference in their entirety.

DETAILED DESCRIPTION

Figure 1:
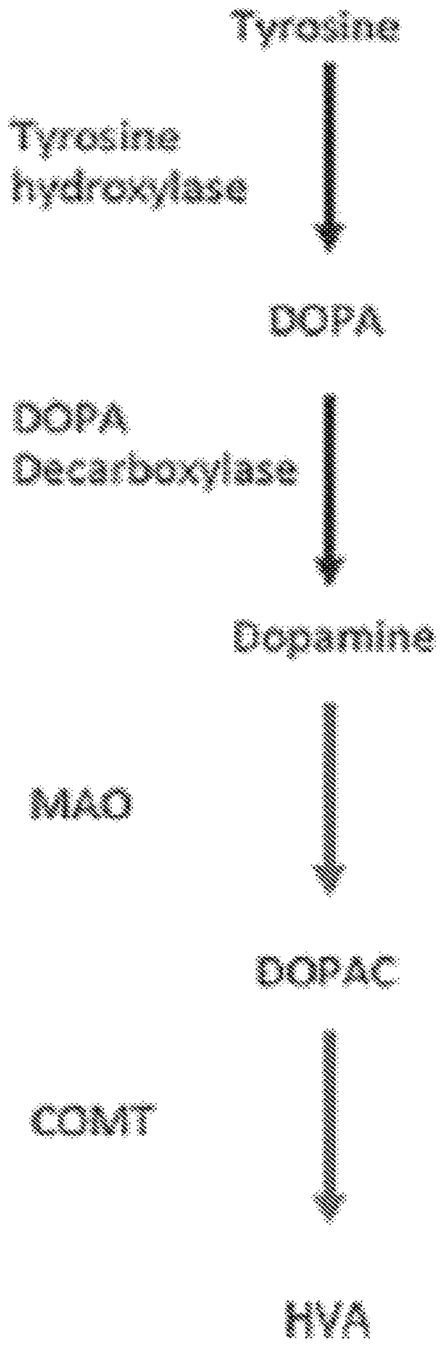
FIG. 1 depicts synthesis and metabolism of dopamine. The enzymes, COMT and MAO are enzymes involved in the metabolism of dopamine.
Figure 2:
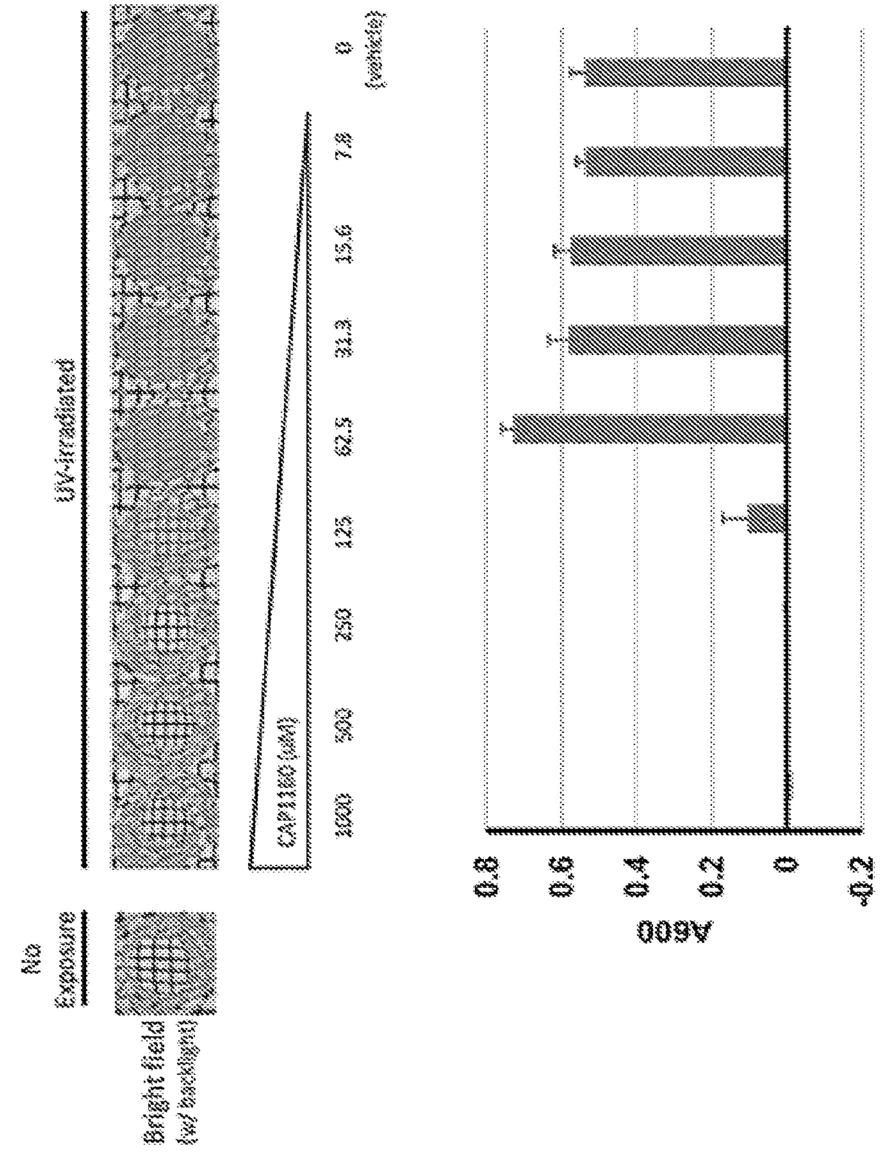
FIG. 2 represents data relating to UVC/$H_2O_2$-induced aggregation of bovine lens extracts, as described in Example 4.

The present disclosure related to compounds useful for the treatment of conditions of the eye, and methods using COMT inhibitors and prodrugs thereof. The inhibitors of COMT and prodrugs can be used as standalone (monotherapy) or in combination with inhibitors of monoamine oxidase for the treatment and/or management of conditions of the eye. In addition, the COMT inhibitors can be used in combination with L-Dopa and/or carbidopa. Further, the COMT inhibitors can also be used in combination with atropine. In some aspects, the COMT inhibitors can be used in combination with one or more of: L-Dopa, carbidopa, and atropine. Described herein are use of COMT inhibitors and their prodrugs for the treatment of conditions of the eye. These compounds may be delivered using one or more a combination of following approaches: (i) topical; (ii) intravitreal; (iii) systemic; (iv) formulated as a device; (v) nanoparticle; (vi) formulated as gel; (vi) coated on to a device (such as glasses and/or contact lenses).

The present disclosure provides compounds of Formula (I) and methods of using these compounds:

(I)

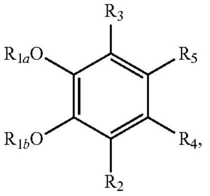

or a solvate or a pharmaceutically acceptable salt thereof, wherein:

$R_{1a}$ and $R_{1b}$ are the same or different, and each of $R_{1a}$ and $R_{1b}$ is independently selected from the group consisting of: hydrogen, $(C_1\text{-}C_3)$alkyl, halo$(C_1\text{-}C_3)$alkyl, $(C_3\text{-}C_6)$ cycloalkyl, halo$(C_3\text{-}C_6)$cycloalkyl, $R^9C{=}O$,

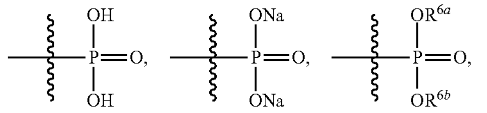

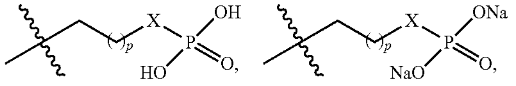

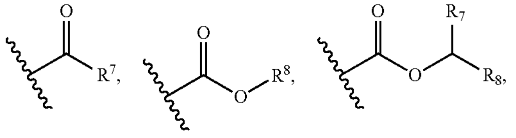

-continued

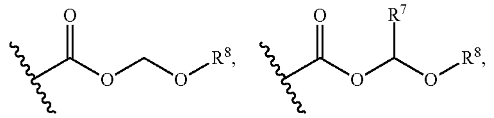

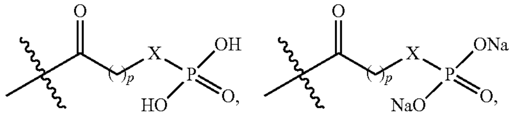

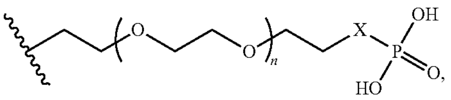

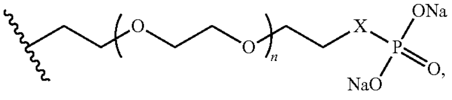

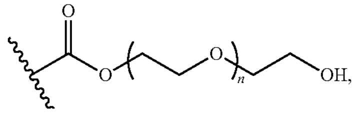

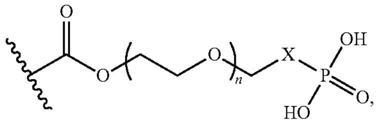

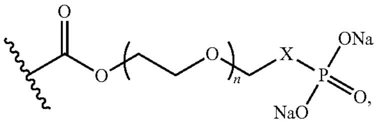 and

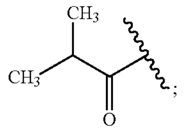

$R_2$ is selected from the group consisting of: hydrogen, $NO_2$, and $(C_1\text{-}C_6)$alkyl;

$R_3$ and $R_4$ are the same or different, and each of $R_3$ and $R_4$ is independently selected from the group consisting of: hydrogen, $(C_1\text{-}C_6)$alkyl, halo$(C_1\text{-}C_6)$alkyl, $(C_3\text{-}C_6)$cycloalkyl, and halo$(C_3\text{-}C_6)$cycloalkyl; and $R_5$ is selected from the group consisting of:

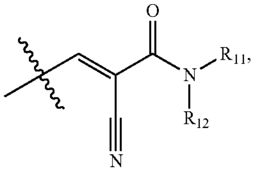

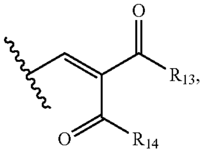

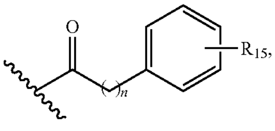

-continued

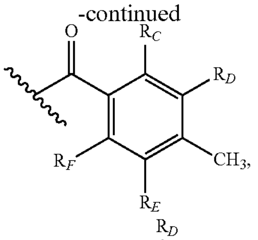

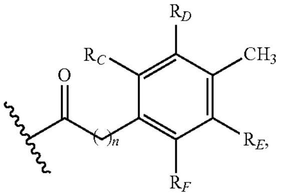

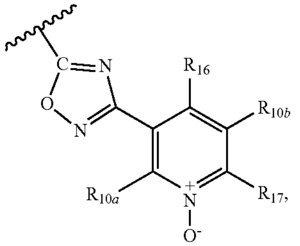

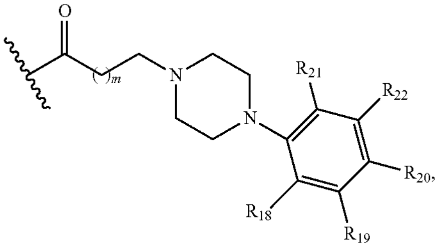

and

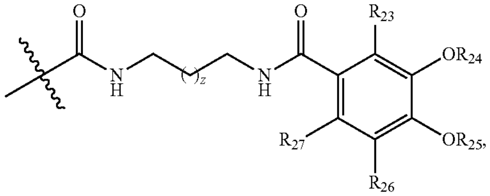

$R_{6a}$, $R_{6b}$, $R_7$ are the same or different and are each independently hydrogen or a $(C_1\text{-}C_6)$alkyl;

$R^8$ is selected from the group consisting of: hydrogen, $(C_1\text{-}C_6)$alkyl, aryl, and

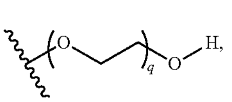

$R^9$ is selected from the group consisting of: $(C_1\text{-}C_6)$alkyl, halo$(C_1\text{-}C_6)$alkyl, $(C_3\text{-}C_6)$cycloalkyl, halo$(C_3\text{-}C_6)$cycloalkyl, aryl, and haloaryl;

$R_{10a}$ and $R_{10b}$ are the same or different, and each of $R_{10a}$ and $R_{10b}$ is a halogen;

$R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{23}$, $R_{26}$, and $R_{27}$, are the same or different, and each is independently selected from the group consisting of: hydrogen, branched or linear $(C_1\text{-}C_6)$alkyl, halo$(C_1\text{-}C_6)$alkyl, $(C_3\text{-}C_6)$cycloalkyl, and halo$(C_3\text{-}C_6)$cycloalkyl;

$R_{22}$ is $CH_3$ or $CF_3$;

$R_{24}$ and $R_{25}$ are the same or different, and each of $R_{24}$ and $R_{25}$ is independently selected from the group consisting of: hydrogen, $(C_1\text{-}C_3)$alkyl, halo$(C_1\text{-}C_3)$alkyl, $(C_3\text{-}C_6)$cycloalkyl, halo$(C_3\text{-}C_6)$cycloalkyl, $R^9C{=}O$,

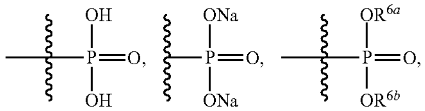

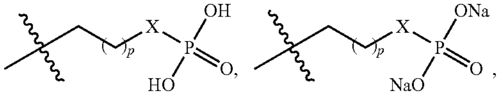

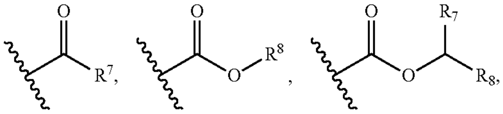

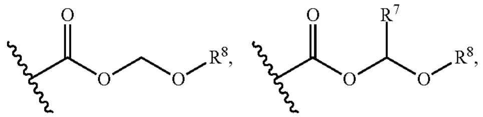

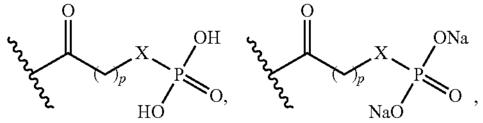

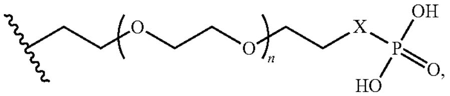

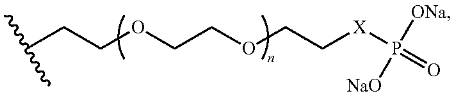

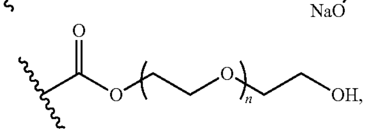

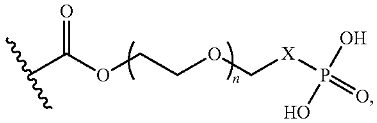

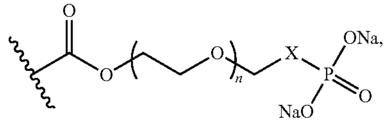

and

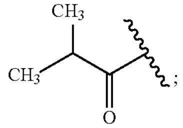

;

$R_C$, $R_D$, $R_E$, and $R_F$ are each the same or different, and each independently are selected from the group consisting of: hydrogen, $(C_1\text{-}C_6)$alkyl, halo$(C_1\text{-}C_6)$alkyl, $(C_3\text{-}C_6)$cycloalkyl, halo$(C_3\text{-}C_6)$cycloalkyl, and hydroxyl;

X is a $C_1$-alkyl, O, or a direct bond;

m and z are each independently a number from 0 to 3, or any range of numbers within 0 to 3;

n and p are each independently a number from 0 to 10, or any range of numbers within 0 to and q is a number from 1 to 10, or any range of numbers within 1 to 10.

In some aspects, at least one of $R_{1a}$, and $R_{1b}$ is not hydrogen. In some aspects, at least one of $R_{1a}$, and $R_{1b}$ is hydrogen. In some aspects, both $R_{1a}$ and $R_{1b}$ are not hydrogen. In some aspects, $R_{1b}$ is hydrogen. In some aspects, $R_{1a}$, and $R_{1b}$ are the same. In some aspects, $R_{1a}$, and $R_{1b}$ are different.

In some aspects, $R_2$, is $NO_2$. In some aspects, $R_2$ is $NO_2$, $R_{1b}$ is hydrogen, and $R_{1a}$ is not hydrogen.

In some aspects, n and p are each independently a number from 0 to 5, or 0 to 4, or 0 to 3, or 0 to 2, or 0 to 1.

In some aspects, the compound is a compound of Formula (I), wherein: (a) if $R_5$ is

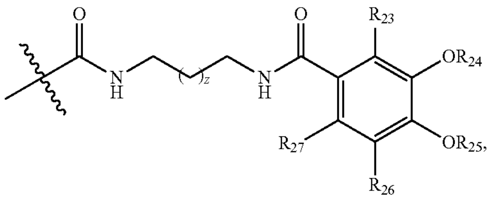

then at least one of $R_{1a}$, $R_{1b}$, $R_{24}$, and $R_{25}$ is not hydrogen, and (b) is $R_5$ is not

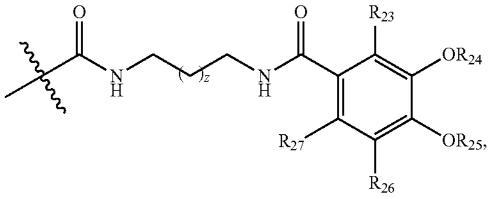

then at least one of $R_{1a}$ and $R_{1b}$ is not hydrogen.

In some aspects, $R_{1a}$ and $R_{1b}$ are the same or different, and each of $R_{1a}$ and $R_{1b}$ is independently selected from the group consisting of: hydrogen, $(C_1\text{-}C_3)$alkyl, halo$(C_1\text{-}C_3)$alkyl, $(C_3\text{-}C_6)$cycloalkyl, halo$(C_3\text{-}C_6)$cycloalkyl, $R^9C{=}O$,

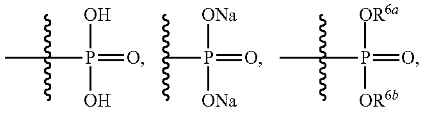

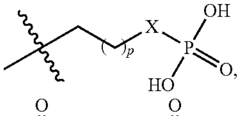

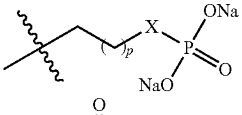

,

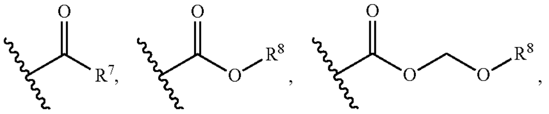

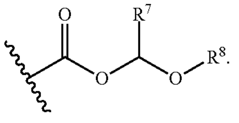

.

In some embodiments, $R^{6a}$, $R^{6b}$, and $R^7$ are each independently hydrogen, $(C_1\text{-}C_6)$alkyl, a $(C_1\text{-}C_5)$alkyl, $(C_1\text{-}C_4)$alkyl, $(C_1\text{-}C_3)$alkyl, $(C_1\text{-}C_2)$alkyl, or a $(C_1)$alkyl.

In some aspects, $R_{1a}$ and $R_{1b}$ are the same or different, and each of $R_{1a}$ and $R_{1b}$ is independently selected from the group consisting of: hydrogen, $(C_1\text{-}C_3)$alkyl, halo$(C_1\text{-}C_3)$alkyl, $(C_3\text{-}C_6)$cycloalkyl, halo$(C_3\text{-}C_6)$cycloalkyl, $R^9C{=}O$,

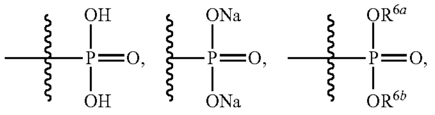

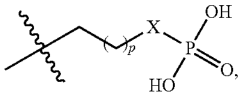

and

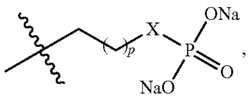

,

In some aspects, one of $R_{1a}$ and $R_{1b}$ is hydrogen, and the other is

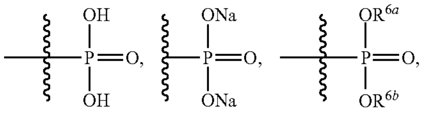

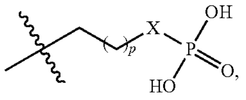

or

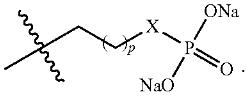

.

In some aspects, $R_5$ is

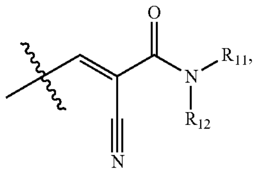

and wherein one or both of $R_{11}$ and $R_{12}$ is $C_2H_5$ or $CH_3$. In some aspects, the one of $R_{11}$ and $R_{12}$ is $C_2H_5$ or $CH_3$ and the other is hydrogen.

In some aspects, $R_5$ is

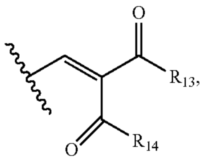

and wherein one or both of $R_{13}$ and $R_{14}$ is $C_2H_5$ or $CH_3$.

In some aspects, $R_5$ is

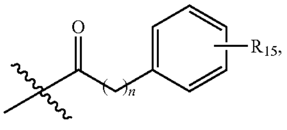

and wherein one or more of $R_4$, $R_{15}$, $R_{16}$, $R_{17}$, $R_{18}$, $R_{19}$, $R_{20}$, $R_{21}$, $R_{23}$, $R_{26}$, and $R_{27}$ is hydrogen. In some aspects, n is a number from 0 to 3.

In some aspects, $R_5$ is

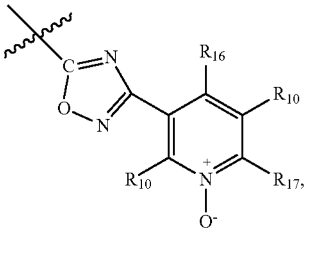

and wherein one or more of $R_4$, $R_{15}$, $R_{16}$, $R_{17}$, $R_{18}$, $R_{19}$, $R_{20}$, $R_{21}$, $R_{23}$, $R_{26}$, and $R_{27}$ is hydrogen.

In some aspects, $R_5$ is

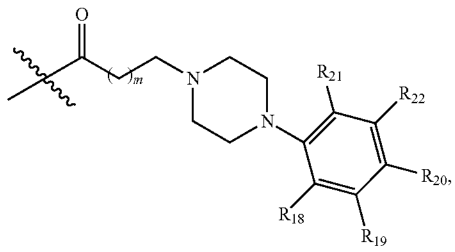

and one or more of $R_4$, $R_{15}$, $R_{16}$, $R_{17}$, $R_{18}$, $R_{19}$, $R_{20}$, $R_{21}$, $R_{23}$, $R_{26}$, and $R_{27}$ is hydrogen. In some aspects m is a number from 0 to 3.

In some aspects, $R_5$ is

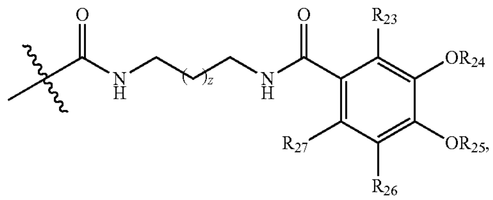

and one or more of $R_4$, $R_{15}$, $R_{16}$, $R_{17}$, $R_{18}$, $R_{19}$, $R_{20}$, $R_{21}$, Rn, $R_{26}$, and $R_{27}$ is hydrogen. In some aspects, z is a number from 0 to 5, or 0 to 3.

In some aspects, X is a direct bond or a $C_1$-alkyl. In some aspects n and p are each independently 0 or 1. In some aspects, $R^{6a}$ and $R^{6b}$ are the same. In some aspects, $R_H$, and $R_J$ are each independently a $(C_1$-$C_3)$alkyl.

In some aspects, at least one of $R_{1a}$ and $R_{1b}$ is

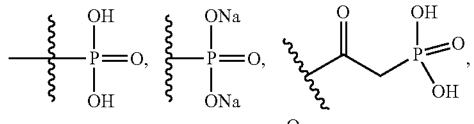

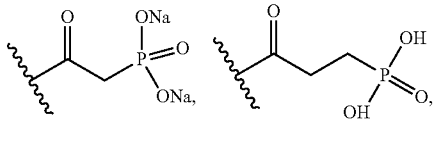

-continued

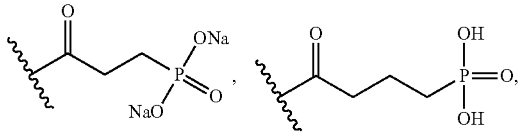

and

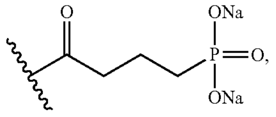

and the other is hydrogen. In some aspects, each of $R_{1a}$ and $R_{1b}$ are independently is

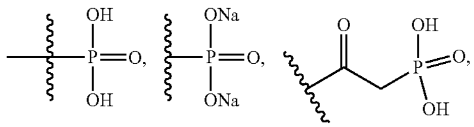

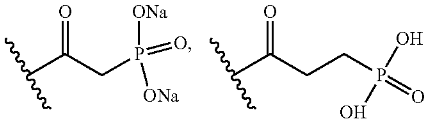

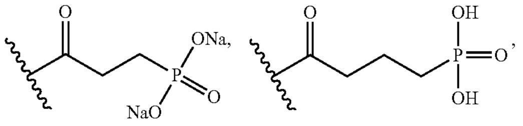

and

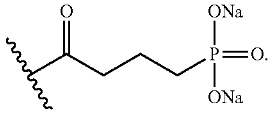

In some aspects, when one or both of $R_{1a}$ and $R_{1b}$ is not hydrogen, the compound is obtained by a process comprising reacting a compound wherein both $R_{1a}$ and $R_{1b}$ are hydrogen to obtain the compound wherein one or both of $R_{1a}$ and $R_{1b}$ is not hydrogen.

The present disclosure provides compounds of Formula (II):

(II)

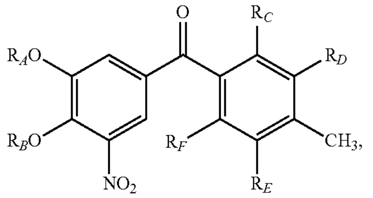

or a solvate or a pharmaceutically acceptable salt thereof, wherein, $R_A$ and $R_B$ are the same or different, and each of $R_A$ and $R_B$ is independently selected from the group consisting of: hydrogen, $R_GC{=}O$,

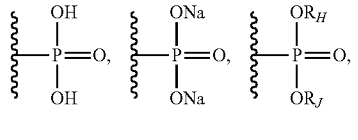

-continued

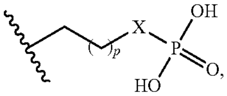
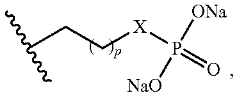
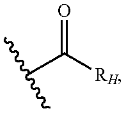
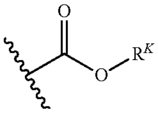
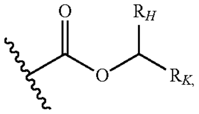
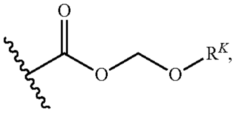
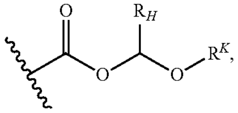
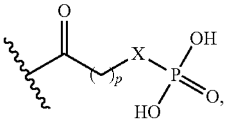
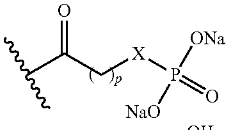
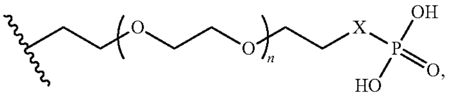
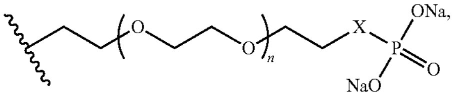
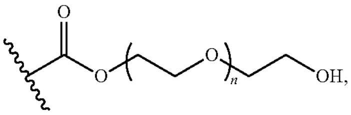
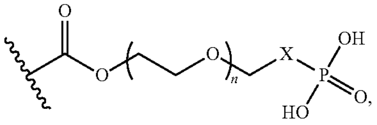
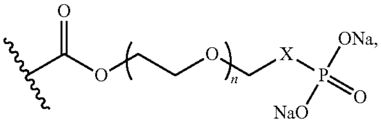
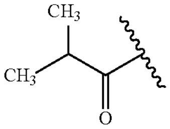;

$R_C$, $R_D$, $R_E$, and $R_F$ are each the same or different, and each independently are selected from the group consisting of: hydrogen, branched or linear $(C_1$-$C_6)$alkyl, halo$(C_1$-$C_6)$alkyl, $(C_3$-$C_6)$cycloalkyl, halo$(C_3$-$C_6)$cycloalkyl, and hydroxyl;

$R_G$ is selected from the group consisting of: branched or linear $(C_1$-$C_6)$alkyl; halo$(C_1$-$C_6)$alkyl; $(C_3$-$C_6)$cycloalkyl; halo$(C_3$-$C_6)$cycloalkyl; aryl; haloaryl; and $R_H$ and $R_J$ are each the same or different, and independently a branched or linear $(C_1$-$C_6)$alkyl, $R_K$ is branched or linear $(C_1$-$C_6)$alkyl, aryl, or

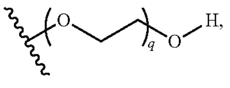

X is a $C_1$-alkyl, O, or a direct bond;

n is a number from 0 to 10, or any range of numbers within 0 to 10;

p is a number from 0 to 10, or any range of numbers within 0 to 10; and q is a number from 1 to 10, or any range of numbers within 0 to 10; and In some aspects, n and p are each independently a number from 0 to 5, or 0 to 4, or 0 to 3, or 0 to 2, or 0 to 1.

In some aspects, the compound is a compound of Formula (II), wherein at least one of $R_A$ and $R_B$ is not hydrogen. In some aspects, both $R_A$ and $R_B$ are not hydrogen. In some aspects, $R_B$ is hydrogen. In some aspects. $R_A$ and $R_B$ are the same. In some aspects. $R_A$ and $R_B$ are different.

In some aspects, $R_A$ and $R_B$ are the same or different, and each of $R_A$ and $R_B$ is independently selected from the group consisting of: hydrogen,

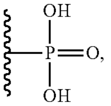
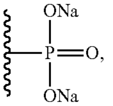
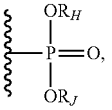
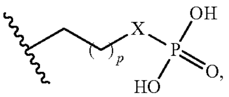
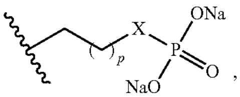
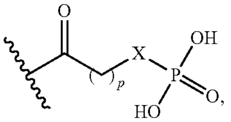
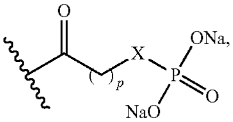
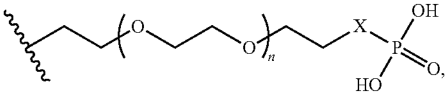
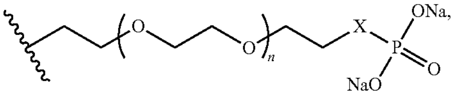
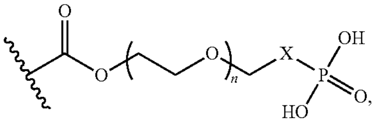 and
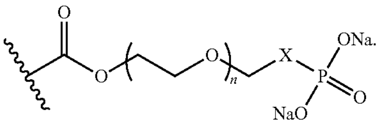

In some aspects, X is a direct bond or a $C_1$-alkyl. In some aspects n and p are each independently 0 or 1. In some aspects. $R_H$ and $R_J$ are the same. In some aspects, $R_H$ and $R_J$ are each independently a $(C_1$-$C_3)$alkyl.

In some aspects, when one or both of $R_A$ and $R_B$ is not hydrogen, the compound is obtained by a process comprising reacting a compound wherein both $R_A$ and $R_B$ are hydrogen, to obtain the compound wherein one or both of $R_A$ and $R_{B1b}$ is not hydrogen.

In some aspects, at least one of $R_A$ and $R_B$ is

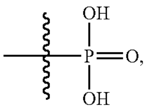
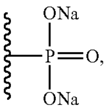
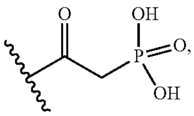
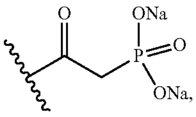
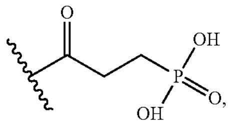
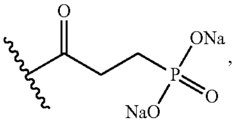
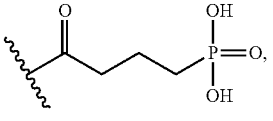 and -continued

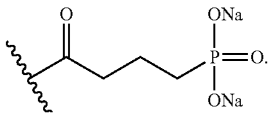

and the other is hydrogen. In some aspects, each of $R_A$ and $R_B$ are independently is

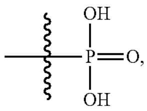, 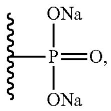, 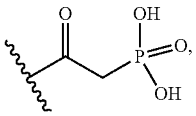,

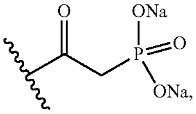, 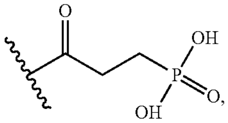,

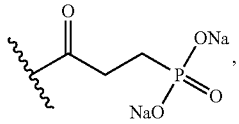, 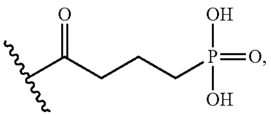, and

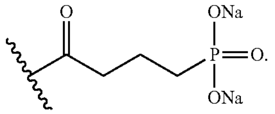

The present disclose provides compounds of Formula (IIa), (IIb), (IIc), (IId), (IIe), (IIf), and (IIg), or solvates or salts there:

(IIa)

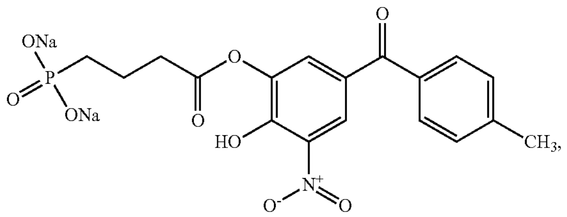

(IIb)

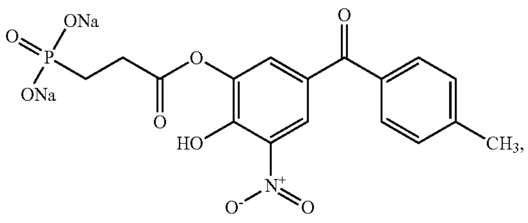

(IIc)

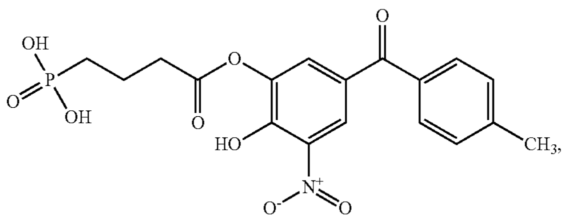

-continued (IId)

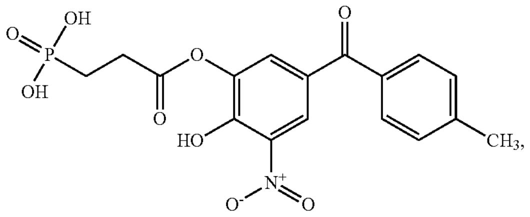

(IIe)

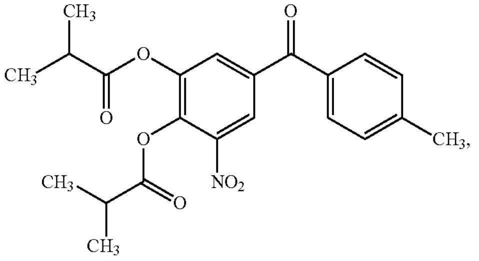

(IIf)

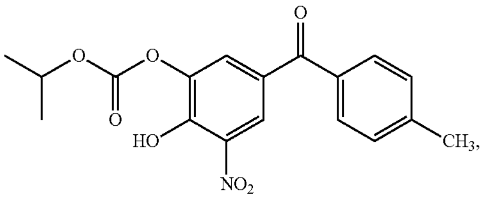

(IIg)

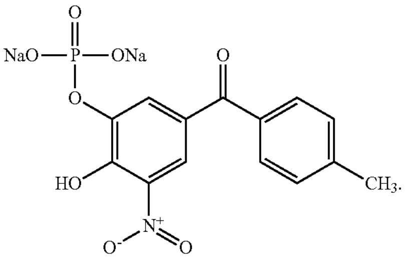

The present disclosure provides compounds of Formula (IIIa), (IVa), (Va), (VIa), (VIIa), (VIIIa), or (IXa) or a solvent or salt thereof (IIIa)

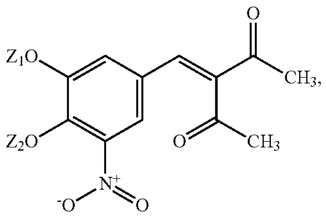

(IVa)

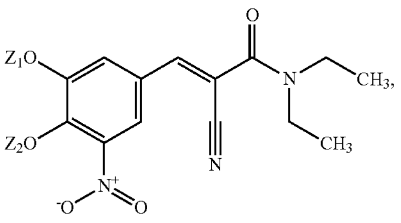

-continued (Va)

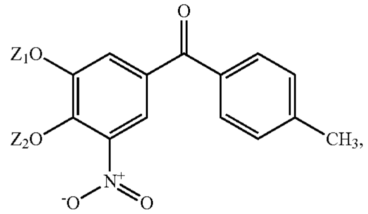

(VIIa)

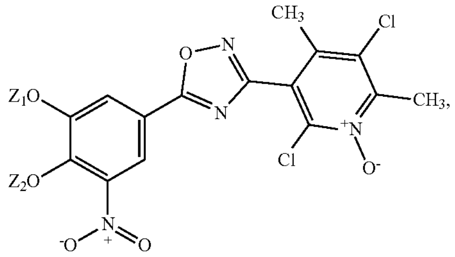

(VIIIa)

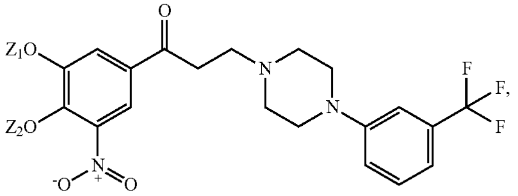

and (IXa)

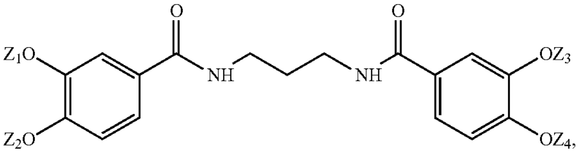

wherein each of $Z_1$, $Z_2$, $Z_3$, and $Z_4$ is the same or different, and each of $Z_1$, $Z_2$, $Z_3$, and $Z_4$ is independently selected from the group consisting of: hydrogen, $(C_1-C_3)$alkyl, halo$(C_1-C_3)$alkyl, $(C_3-C_6)$cycloalkyl, halo$(C_3-C_6)$cycloalkyl, $R^9C{=}O$,

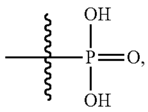 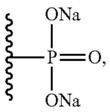 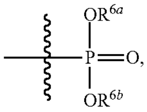

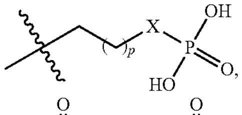 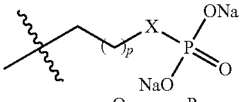 ,

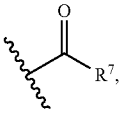 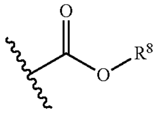 , 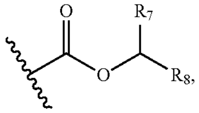

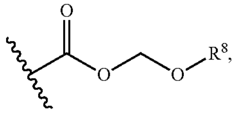 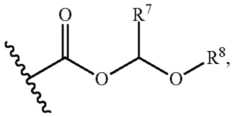

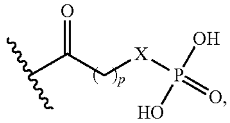 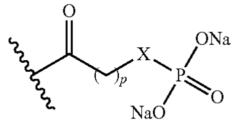 ,

-continued

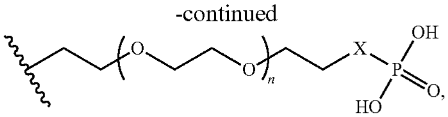

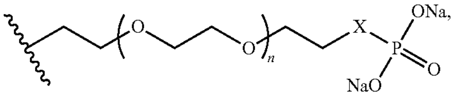

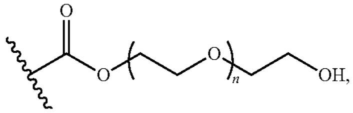

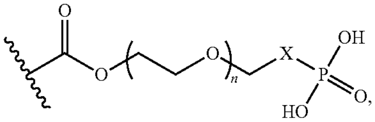

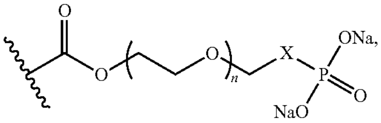 and

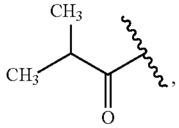

$R^{6a}$, $R^{6b}$, $R^7$ are the same or different and are each independently hydrogen or a $(C_1-C_6)$alkyl;

$R^8$ is selected from the group consisting of: hydrogen, $(C_1-C_6)$alkyl, aryl, and

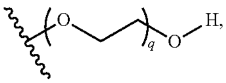

$R^9$ is selected from the group consisting of: $(C_1-C_6)$alkyl, halo$(C_1-C_6)$alkyl, $(C_3-C_6)$cycloalkyl, halo$(C_3-C_6)$cycloalkyl, aryl, and haloaryl;

X is a $C_1$-alkyl, O, or a direct bond;

m is a number from 0 to 3;

n and p are each independently a number from 0 to 10; and q is a number from 1 to 10, In some aspects, at least one of $Z_1$ and $Z_2$ is not hydrogen. In some aspects, at least one of $Z_1$ and $Z_2$ is hydrogen. In some aspects, both $Z_1$ and $Z_2$ are not hydrogen. In some aspects, $Z_2$ is hydrogen. In some aspects, $Z_2$ are the same. In some aspects, $Z_1$ and $Z_2$ are different.

In some aspects, $Z_1$ and $Z_2$ are each independently selected from the group consisting of:

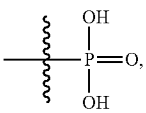 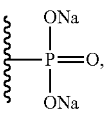 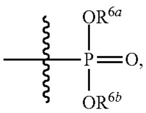

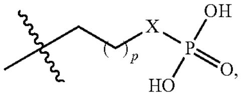 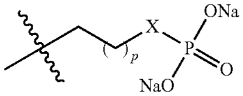 ,

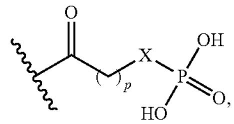 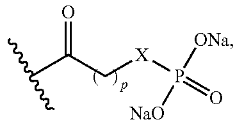

-continued

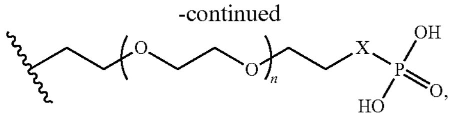

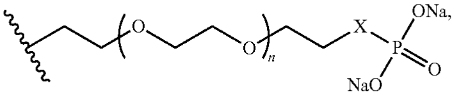

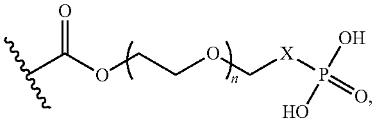

and

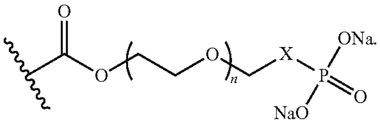

In some aspects, one of $Z_1$ and $Z_2$ is hydrogen and the other is selected from the group consisting of:

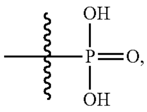

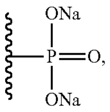

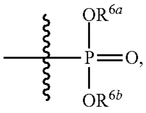

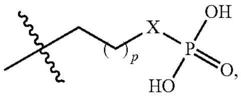

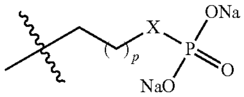

,

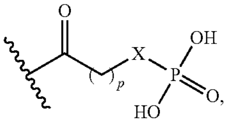

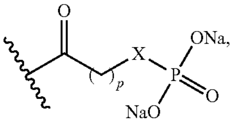

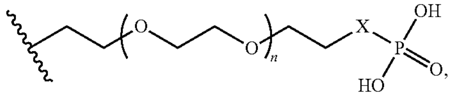

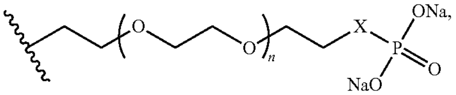

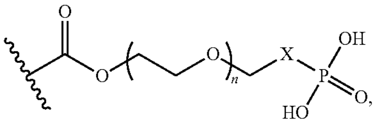

and

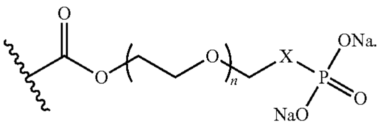

In some aspects, In some aspects, n and p are each independently a number from 0 to 5, or 0 to 4, or 0 to 3, or 0 to 2, or 0 to 1.

In some aspects, wherein the compound is a compound of Formula (IXa), at least one of $Z_1$, $Z_2$, $Z_3$, and $Z_4$ is not hydrogen. In some aspects, at least one $Z_1$, $Z_2$, $Z_3$, and $Z_4$ is hydrogen. In some aspects, one, two, or three of $Z_1$, $Z_2$, $Z_3$, and $Z_4$ is hydrogen. In some aspects, none of $Z_1$, $Z_2$, $Z_3$, and $Z_4$ is hydrogen. In some aspects, one, two, three, or four of $Z_1$, $Z_2$, $Z_3$, and $Z_4$ is the same. In some aspects, one, two, three, or four of $Z_1$, $Z_2$, $Z_3$, and $Z_4$ is different.

In some aspects, the compounds of Formula (IIIa), (IVa), (Va), (VIa), (VIIa), (VIIIa), or (IXa) or a solvent or salt are obtained by reacting the compounds of Formulas (III), (IV), (V), (VI), (VII), (VIII), or (IX), respectively:

(III)

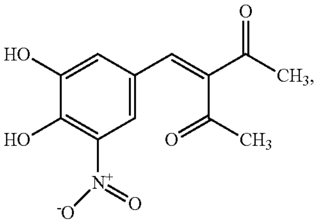

(IV)

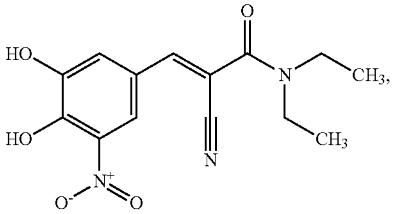

(V)

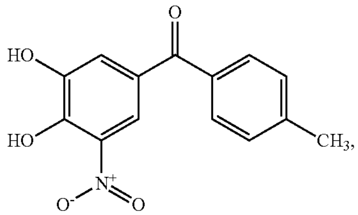

(VI)

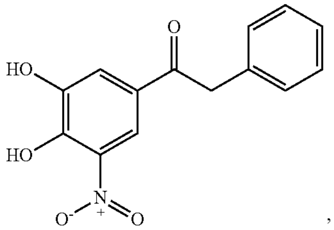

, (VII)

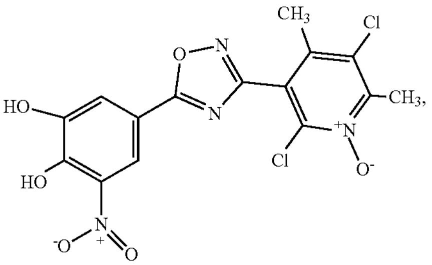

(VIII)

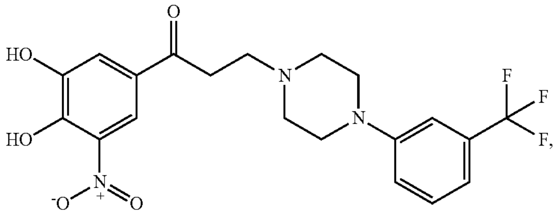

(IX)

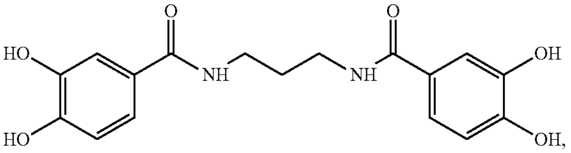

or a solvent or salt there. In some aspects, the compounds of Formulas (III), (IV), (V), (VI), (VII), (VIII), or (IX), can be used as a starting material to prepare the compounds of Formula (IIIa), (IVa), (Va), (VIa), (VIIa), (VIIIa), or (IXa), respectively. The compounds may be obtained as described in any of the following, or obtained using starting compounds described in the following, which are each incorporated by reference in their entirety: Canadian Patent No. 2,342,634; Learmonth et al. Synthesis and biological evaluation of a novel series of "ortho-nitrated" inhibitors of catechol-O-methyltransferase. *J Med Chem.* 2005 Dec. 15; 48(25):8070-8; Backstrom et al. Synthesis of some novel potent and selective catechol O-methyltransferase inhibitors. *J Med Chem.* 1989 April; 32(4):841-6; Ma et al. Structure-based drug design of catechol-O-methyltransferase inhibitors for CNS disorders. *Br J Clin Pharmacol.* 2014; 77(3):410-420; and Bailey et al. Synthesis and evaluation of bifunctional nitrocatechol inhibitors of pig liver catechol-O-methyltransferase. *Bioorg Med Chem.* 2005 Oct. 15; 13(20):5740-9.

In some aspects, compounds of the present disclosure that are pro-drugs may be made by a process, such as the one shown below, which is a representative scheme. The starting materials and reagents used for reacting with the —OH group are merely examples and each may be selected as appropriate based on the desired end product.

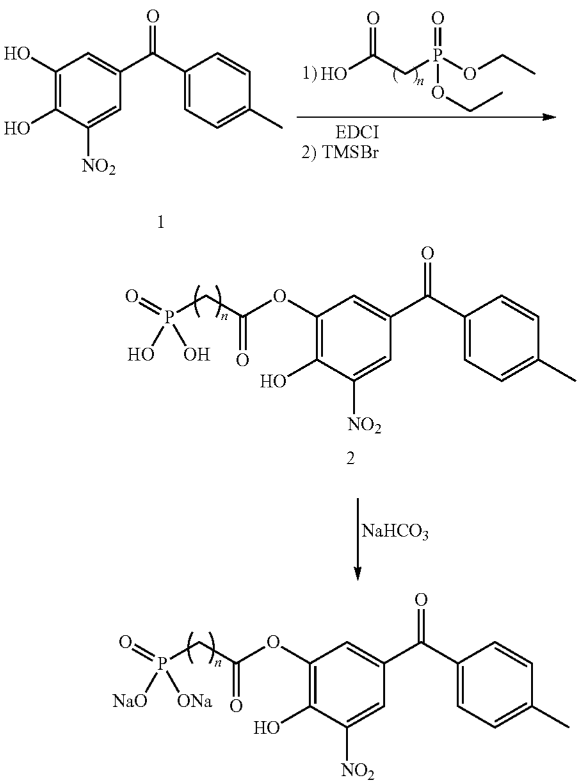

1

2

3

The present disclosure provides the following compounds, or a salt or solvate thereof:

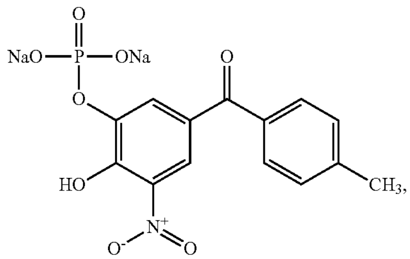
,

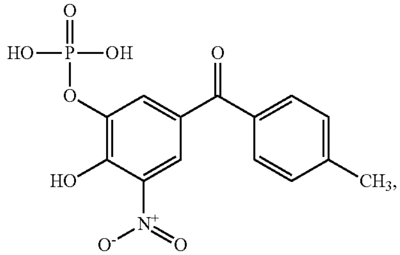
,

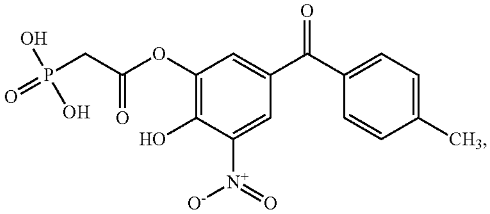
,

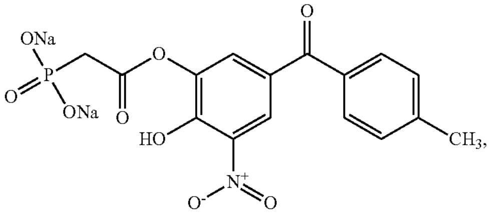
,

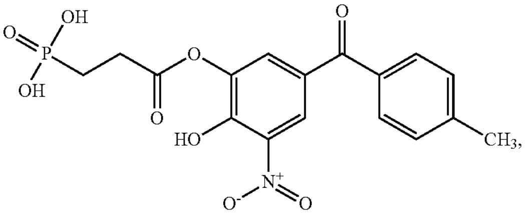
,

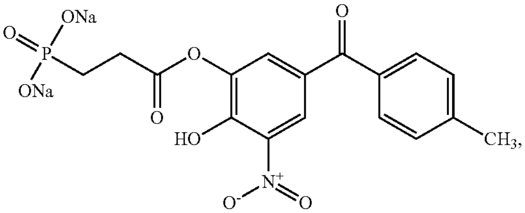
,

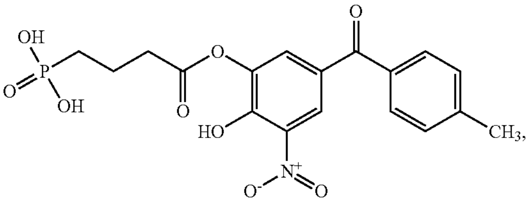
, and

-continued

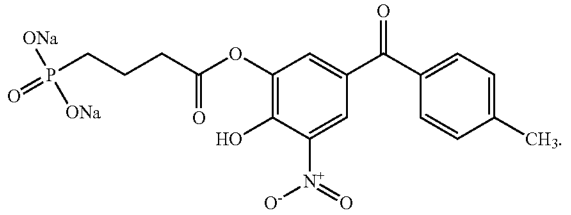

The present disclosure provides pharmaceutical compositions comprising the above compound and a pharmaceutically acceptable excipient. The present disclosure also provides methods of using the above compounds, comprising administration to a subject in need thereof.

The present disclosure provides a pharmaceutical composition comprising any of the compounds, or solvents of salts thereof, in the disclosure, and a pharmaceutically acceptable excipient. In some aspects, the pharmaceutical composition comprises a compound of Formula (I), (II), (III), (IV), (V), (VI), (VII), (VIII), (IX), (IIa), (IIb), (IIc), (IId), (IIe), (IIf), (IIg), (IIIa), (IVa), (Va), (VIa), (VIIa), (VIIIa), or (IXa). In some aspects, the pharmaceutical composition further comprises one or more additional agents, and the methods discussed herein provide for co-administration of one or more additional agents. In some aspects, the additional agent is a compound suitable for treating, preventing, reducing the occurrence of, slowing the progression of, or reducing, ameliorating, or alleviating the symptoms associated with a condition or disorder associated with the eye, including but not limited to presbyopia, cataract, transthyretin (TTR)-associated amyloidosis, and myopia, and any other condition that would benefit from administration of a COMT inhibitor or a compound that has an inhibitory effect on COMT. In some aspects, the additional agent is a monoamine oxidase inhibitor (MAOI). Examples of MAOIs include, but are not limited to: isocarboxazid, selegiline, moclobemide, rasagiline, clorgyline, benmoxin, echinopsidine, mebanazine, metralindole, paragyline, phenelzine, and tranylcyclopramine. In some aspects, the COMT inhibitor or compound having an additional effect on COMT, or the additional agent, is L-Dopa and/or carbidopa. In some aspects, the additional agent is a COMT inhibitor or a further COMT inhibitor or any compound having an inhibitory effect on COMT. In some aspects, the additional agent is nitecapone, entacapone, nebicapone, tolcapone, BIA 3-3335 (1-(3,4-Dihydroxy-5-nitrophenyl)-3-{4-[3-(trifluoromethyl) phenyl]-1-piperazinyl}-1-propanone dihydrochloride), or bifunctional inhibitor compounds such as N,N'-(propane-1, 3-diyl)bis(3,4-dihydroxybenzamide). In some aspects, the additional agent is atropine. In some aspects, the additional agent is a non-steroidal anti-inflammatory agent.

In some aspects, the present disclosure provides a pharmaceutical composition comprising: a compound of Formula (I), (II), (III), (IV), (V), (VI), (VII), (VIII), (IX), (IIa), (IIb), (IIc), (IId), (IIe), (IIf), (IIg), (IIIa), (IVa), (Va), (VIa), (VIIa), (VIIIa), (IXa); atropine; and one or more pharmaceutically acceptable excipients. In some aspects, the additional agent is in pro-drug form or not in pro-drug form.

The present disclosure provides a method of treating, preventing, reducing the occurrence of, slowing the progression of, or reducing, ameliorating, or alleviating the symptoms associated with a condition selected from the group consisting of: presbyopia, cataract, transthyretin (TTR)-associated amyloidosis, myopia, or other conditions or disorders associated with the eye in a subject in need thereof, comprising administering any of the compounds, or solvents of salts thereof, in the disclosure, to the subject. In some aspects, the present disclosure provides a method of treating, preventing, reducing the occurrence of, slowing the progression of, or reducing, ameliorating, or alleviating the symptoms associated with a condition selected from the group consisting of: presbyopia, cataract, transthyretin (TTR)-associated amyloidosis, myopia, or other conditions or disorders associated with the eye in a subject in need thereof, comprising administering any of compounds of Formula (I), (II), (III), (IV), (V), (VI), (VII), (VIII), (IX), (IIa), (IIb), (IIc), (IId), (IIe), (IIf), (IIg), (IIIa), (IVa), (Va), (VIa), (VIIa), (VIIIa), (IXa), or a solvent or salt thereof to the subject. In some aspects, the present disclosure provides methods of reducing or inhibiting the formation of, or dissolving high molecular weight aggregates of human α-A-crystallin, or to treat, prevent, or reduce the occurrence of or to reduce, ameliorate, or alleviated symptoms associated with conditions relating to human α-A-crystallin and conditions including but not limited to: transthyretin (TTR)-associated amyloidosis, Prion, Creutzfeldt-Jakob, Gerstmann-Sträussler-Scheinker disease and Ankyloblepharon-ectodermal dysplasia-cleft lip/palate syndrome, comprising administering an effective amount of any of the compounds of the present disclosure.

In some aspects, myopia includes but is not limited to high non-pathologic-myopia, pathological myopia, pseudomyopia, deprived myopia (FDM) and lens induced myopia (LIM).

In some aspects, the compound may be administered as monotherapy or with an additional agent. In some aspects, the present disclosure provides methods of administering a compound of the present disclosure and an additional agent, and methods of administrating a pharmaceutical composition comprising a compound of the present disclosure, an additional agent, and one or more pharmaceutically acceptable excipients. In some aspects, the present disclosure provides a method for treating, preventing, reducing the occurrence of, slowing the progression of, or reducing, ameliorating, or alleviating the symptoms associated with a condition of the eye, including but not limited to myopia, in a subject in need thereof, comprising administering to the subject any of the compounds of the present disclosure and one or more additional agents, including but not limited to atropine. In some aspects, the co-administration with one or more additional agents may provide synergistic effects. In some aspects, the co-administration with atropine may provide synergistic effects.

In some aspects, the present disclosure provides a method for treating, preventing, reducing the occurrence of, slowing the progression of, or reducing, ameliorating, or alleviating the symptoms associated with a condition to a subject in need thereof, comprising administering to the subject a COMT inhibitor or any compound having an inhibitory effect on COMT. In some aspects, the condition is a condition of the eye. In some aspects, the condition of the eye is myopia, including but not limited to high non-pathologic-myopia, pathological myopia, pseudomyopia, deprived myopia (FDM) and lens induced myopia (LIM). In some aspects, the condition of the eye is presbyopia, cataract, transthyretin (TTR)-associated amyloidosis. In some aspects, the condition is a condition relating to human α-A-crystallin and conditions including but not limited to: transthyretin (TTR)-associated amyloidosis, Prion, Creutzfeldt-Jakob, Gerstmann-Sträussler-Scheinker disease and Ankyloblepharon-ectodermal dysplasia-cleft lip/palate syndrome In some aspects, the COMT inhibitor or compound having an inhibitory effect on COMT may or may not be a pro-drug. In some aspects, the present disclosure provides a method for treating, preventing, reducing the occurrence of, slowing the progression of, or reducing, ameliorating, or alleviating the symptoms associated with a condition to a subject in need thereof, comprising administering to the subject a pharmaceutical composition comprising a COMT inhibitor or any compound having an inhibitory effect on COMT, and one or more pharmaceutically acceptable excipients.

In some aspects, the present disclosure provides a method for treating, preventing, reducing the occurrence of, slowing the progression of, or reducing, ameliorating, or alleviating the symptoms associated with a condition to a subject in need thereof, comprising administering to the subject L-dopa and/or carbidopa, or a pharmaceutical composition comprising L-dopa and/or carbidopa and one of more pharmaceutically acceptable excipients. In some aspects, the condition is a condition of the eye, including but not limited to presbyopia, cataract, transthyretin (TTR)-associated amyloidosis, and myopia In some aspects, the condition is a condition relating to human α-A-crystallin and conditions including but not limited to: transthyretin (TTR)-associated amyloidosis, Prion, Creutzfeldt-Jakob, Gerstmann-Sträussler-Scheinker disease and Ankyloblepharon-ectodermal dysplasia-cleft lip/palate syndrome.

In some aspects, the present disclosure provides a method of treating, preventing, reducing the occurrence of, slowing the progression of, or reducing, ameliorating, or alleviating the symptoms associated with a condition, such as a condition of the eye, including but not limited to presbyopia, cataract, transthyretin (TTR)-associated amyloidosis, and myopia in a subject in need thereof, comprising administering to the subject a compound of Formula (I), (II), (III), (IV), (V), (VI), (VII), (VIII), (IX), (IIa), (IIb), (IIc), (IId), (IIe), (IIf), (IIg), (IIIa), (IVa), (Va), (VIa), (VIIa), (VIIIa), (IXa); and atropine. In some aspects, the present disclosure provides a method of treating, preventing, reducing the occurrence of, slowing the progression of, or reducing, ameliorating, or alleviating the symptoms associated with a condition of the eye, including but not limited to myopia, in a subject in need thereof, comprising administering to the subject a pharmaceutical composition comprising: a compound of Formula (I), (II), (III), (IV), (V), (VI), (VII), (VIII), (IX), (IIa), (IIb), (IIc), (IId), (IIe), (IIf), (IIg), (IIIa), (IVa), (Va), (VIa), (Vila), (VIIIa), (IXa); atropine; and one or more pharmaceutically acceptable excipients. In some aspects, the condition is myopia.

In some aspects, the present disclosure provides methods of administering any of the compounds of the present disclosure and one or more of: atropine, L-Dopa, and carbidopa. In some aspects, the present disclosure provides methods of administering any of the compounds of the present disclosure, atropine, and optionally L-Dopa and/or carbidopa. In some aspects, the present disclosure provides pharmaceutical compositions comprising a compound of the present disclosure, one or more pharmaceutically acceptable exciepints, and further comprising one or more of: atropine, L-Dopa, and carbidopa. In some aspects, the present disclosure provides pharmaceutical compositions comprising a compound of the present disclosure, atropine, one or more pharmaceutically acceptable excipients, and optionally L-Dopa and/or carbidopa. In some aspects, the combination of one or more of: atropine, L-Dopa, and/or carbidopa provide a synergistic effect. In some aspects, the combination of any of the compounds of the presently claimed invention and one or more of: atropine, L-Dopa, and/or carbidopa provide a synergistic effect. In some aspects, the combination of a compound of Formula (IVa), (Va), (VIa), (VIIa), (VIIIa), (IXa) with one or more of: atropine, L-Dopa, and/or carbidopa provide a synergistic effect.

In some aspects, the compounds of the present disclosure are administered in an amount effective for treating, preventing, reducing the occurrence of, slowing the progression of, or reducing, ameliorating, or alleviating the symptoms associated with a condition selected from the group consisting of: presbyopia, cataract, transthyretin (TTR)-associated amyloidosis, myopia, or other conditions or disorders associated with the eye. In some aspects, pharmaceutical compositions comprise a compound of the present disclosure in an effective amount.

In some aspects, the compounds of the present disclosure may be administered through any route of administration, including but not limited to oral, nasal, intranasal, intramuscular, intravenous, subcutaneous, rectal, sublingual, intrathecal, transdermal, intraocularly, inhalation or other topical. In some aspects, the compounds of the present disclosure are administrated intraocularly or topically to the eye. In some aspects, the pharmaceutical composition is an ophthalmic solution or suspension comprising a compound of the present disclosure and one or more pharmaceutically acceptable excipients suitable for administration to the eye. In some aspects, an amount effective to reduce or inhibit the formation of, or dissolve high molecular weight aggregates of human α-A-crystallin, or to treat, prevent, or reduce the occurrence of or to reduce, ameliorate, or alleviated symptoms associated with conditions relating to human α-A-crystallin. In some aspects, the conditions include but are not limited to: transthyretin (TTR)-associated amyloidosis, Prion, Creutzfeldt-Jakob, Gerstmann-Straussler-Scheinker disease and Ankyloblepharon-ectodermal dysplasia-cleft lip/palate syndrome Methods used to deliver compounds described herein to the eye include, but are not limited to: (i) topical, (ii) (iii) subconjunctival, (iv) intravitreal, (v) systemic, (vi) using a device using a formulation suitable for the device (vii) as nanoparticles (vii) as a gel with suitable formulation, (viii) coated on to a device (such as contact lenses).

With regard to topical administration, such administration is typically accomplished using eye drops. Contact time on the eye surface is short, but can be prolonged using specific formulations, e.g., gels, gelifying formulations, ointments, and inserts. Typically, the basic nature of the solution containing the drug composition is aqueous and as such, agents designed to increase the viscosity of the solution may be employed. Such agents include, for example, hydroxypropyl methylcellulose, carbopol, polyvinyl alcohol, and the like.

Traditionally subconjunctival injections have been used to deliver drugs at increased levels to the uvea. This mode of administration can be used to deliver drugs in controlled release formulations to the posterior segment and to guide the healing process after surgery.

With regard to intravitreal administration, direct drug administration into the vitreous offers the advantage of more straightforward access to the vitreous and retina. Delivery from the vitreous to the choroid is more complicated, however, due to the hindrance by the RPE (Retinal Pigment Epithelium) barrier. Small molecules are able to diffuse rapidly in the vitreous but the mobility of large molecules, particularly those that are positively charged, is restricted. An injectable composition suitable for intraocular injection typically comprises a solution of the drug or a fine particle suspension, which may enable sustained delivery to the eye.

Formulations are usually aqueous and may commonly include solubilization enhancers such as, but not limited to, polyvinyl alcohol, Tween 80, solutel, cremophore, and cyclodextrin. These solubilization enhancers may be used in combination. The formulation is typically in the pH range of 3-8, which is regarded as acceptable for intravitreal formulations. To achieve an acceptable pH, buffering systems are sometimes used. These include but are not limited to citrate and phosphate based buffering systems. The tonicity of the intravitreal formulation may be adjusted to remain within a desirable range which typically would be 250-360 mOsm/kg. Adjustment of tonicity may be achieved for example by addition of sodium chloride. Typically, intravitreal formulations are produced by sterile manufacture for single use. Preserved formulations can be used, for example, formulations containing a preservative such as benzoyl alcohol. The dose of the active agent in the compositions of the invention will depend on the nature and degree of the condition, the age and condition of the patient and other factors known to those skilled in the art. Administration can be either as a single injection with no further dosing or multiple injections.

With respect to systemic administration, systemic medication is required for posterior segment therapy and to complement topical therapy for the anterior segment. The posterior segment always requires systemic therapy, because most topical medications do not penetrate to the posterior segment Retrobulbar and orbital tissues are treated systemically.

In some aspects, the present disclosure provides a method of treating conditions of the eye that requires administration of an effective amount of a composition comprising a compound described herein, the compound being present in a prodrug form, or being converted to a prodrug form. Prodrug formulations use pharmacologically inactive derivatives of drug molecules that are better able to penetrate the cornea (e.g., they are more lipophilic) than the standard formulation of the drug. See review by Brian G. Short, *Toxicologic Pathology,* 36:49-62, 2008. As described in the review and the references cited therein, within the cornea or after corneal penetration, the prodrug is either chemically or enzymatically metabolized to the active parent compound. Enzyme systems identified in ocular tissues include esterases, ketone reductase, and steroid 6β-hydroxylase.

Most prodrugs are delivered conventionally by topical application such as antiviral prodrugs ganciclovir and acyclovir, although ganciclovir has also been delivered intravitreally by injection or as a nonbiodegradable reservoir. Delivery of a drug with a nonnatural enzyme system in the cornea has been achieved with topical 5-fturocytosine, a prodrug of 5-fluorouracil, administered after subconjunctival transplantation of cells containing the converting enzyme cytosine deaminase. Increased corneal penetration into the anterior segments can be achieved with the addition of permeability enhancers to the drug formulation. Surfactants, bile acids, chelating agents, and preservatives have all been used. Cyclodextrins, cylindrical oligonucleotides with a hydrophilic outer surface and a lipophilic inner surface that form complexes with lipophilic drugs, are among the more popular permeability enhancers, They increase chemical stability and bioavailability and decrease local irritation, and they have been used with corticosteroids, choloramphenicol, diclofenac, cyclosporine, and sulfonamide carbonic anhydrase inhibitors. The present invention includes small molecule inhibitors that are synthesized as prodrugs such that they have a better ability to permeate the cornea.

The terms "halo" and "halogen," as used herein refer to an atom selected from fluorine (fluoro, —F), chlorine (chloro, —Cl), bromine (bromo, —Br), and iodine (iodo, —I).

The term "alkyl," used alone or as a part of a larger moiety such as e.g., "haloalkyl," means a saturated monovalent straight or branched, substituted or unsubstituted hydrocarbon radical having, unless otherwise specified, 1-10 carbon atoms and includes, for example, methyl, ethyl, n-propyl, isopropyl, n-butyl, see-butyl, isobutyl, tert-butyl, n-pentyl n-hexyl, n-heptyl, n-octyl, n-nonyl, n-decyl, and the like. "Monovalent" means attached to the rest of the molecule at one point.

The terms "cycloalkyl" used alone or as part of a larger moiety, refers to a saturated cyclic aliphatic monocyclic, bicyclic or tricyclic substituted or unsubstituted ring system as described herein, having from, unless otherwise specified, 3 to 10 carbon ring atoms. Monocyclic cycloalkyl groups include. without limitation, cyclopropyl, cyclobutyl, cyclopentyl, cyclopentenyl, cyclohexyl, cyclohexenyl, cycloheptyl cycloheptenyl, and cyclooctyl. Bicyclic cycloalkyl groups include e.g., cycloalkyl group fused to another cycloalkyl group, such as decalin or a cycloalkyl group fused to an and group (e.g., phenyl) or heteroaryl group, such as tetrahydronaphthalenyl, indanyl, 5,6,7,8-tetrahydroquinoline, and 5,6,7,8-tetrahydroisoquinoline. An example of a tricyclic ring system is adamantane. It will be understood that the point of attachment for bicyclic cycloalkyl groups can be a tether on the cycloalkyl portion or on the aryl group (e.g., phenyl) or heteroaryl group that results in a stable structure. It will be further understood that when specified, optional substituents on a cyloalkyl may be present on any substitutable position and, include, e.g., the position at which the cycloalkyl is attached.

The term "heterocyclyl" means a 4-, 5-, 6- and 7-membered saturated or partially unsaturated substituted or unsubstituted heterocyclic ring containing 1 to 4 heteroatoms independently selected from N, O, and S. The terms "heterocycle," "heterocyclyl," "heterocyclyl ring," "heterocyclic group," "heterocyclic moiety," and "heterocyclic radical" may be used interchangeably. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyrrolidonyl, piperidinyl, oxetanyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, and tetrahydropyrimidinyl. A heterocylyl group may be mono- or bi-cyclic. Unless otherwise specified, bicyclic heterocydyl groups include, e.g., unsaturated or saturated heterocyclic radicals fused to another unsaturated heterocyclic radical or aromatic or heteroaryl ring, such as for example, chronmnyl, 2,3-dihydrobenzo[b][1,4]dioxioyl, tetrahydronaphthyridioyl, dihydropyrrolotriazolyl, imidazopynmidinyl, quinolinonyl, dioxaspirodecanyl. It will be understood that the point of attachment for bicyclic heterocydyl groups can be on the heterocyclyl group or aromatic ring that results in a stable structure. It will also be understood that when specified, optional substituents on a heterocyclyl group may be present on any substitutable position and, include, e.g., the position at which the heterocyclyl is attached.

The term "heteroaryl" used alone or as part of a larger moiety as in "heteroarylalkyl", "heteroarylalkoxy", or "heteroatylaminoalkyl", refers to a 5-10-membered substituted or unsubstituted aromatic radical containing 1-4 heteroatoms selected from N, O, and S and includes, for example, thienyl, furanyl, pyrrolyl, imidazolyl pyrazolyl, triazolyl, tetrazolyl, oxazolyl, isoxazolyl, oxadiazolyl, thiazolyl, isothiazolyl, thiadiazolyl, pyridyl, pyridazioyl, pyrimidinyl, pyrazinyl, indolizinyl purinyl, naphthyridinyl, and pteridinyl. The term "heteroaryl" may be used interchangeably with the terms "heteroaryl ring", "heteroaryl group", or "heteroaromatic". The terms "heteroaryl" and "heteroar-", as used herein, also include groups in which a heteroaromatic ring is fused to one or more aryl rings, where the radical or point of attachment is on the heteroaromatic ring. Nonlimiting examples include indolyl, indazolyl, benzimidazolyl, benzthiazolyl, quinolyl, quinazolinyl, and quinoxalinyl. A heteroaryl group may be mono- or bicyclic. It will be understood that when specified, optional substituents on a heteroaryl group may be present on any substitutable position and, include, e.g., the position at which the heteroaryl is attached. As used herein, the term "aryl", used done or in conjunction with other terms, refers to a 6-14 membered aromatic ring containing only ring carbon atoms. The aryl ring may be monocyclic, bicyclic or tricyclic. Non-limiting examples include phenyl, naphthyl or anthracenyl, and the like. It will also be understood that when specified, optional substituents on an aryl group may be present on any substitutable position. The aryl group may be unsubstituted or mono- or di-substituted.

As used herein the terms "subject" and "patient" may be used interchangeably, and means a mammal in need of treatment, e.g., companion animals (e.g., dogs, eats, and the like), farm animals (e.g., cows, pigs, horses, sheep, goats and the like) and laboratory animals (e.g., rats, mice, guinea pigs and the like). Typically, the subject is a human in need of treatment.

The compounds of the present disclosure may be present in the form of pharmaceutically acceptable salts. For use in medicines, the salts of the compounds of the invention refer to non-toxic "pharmaceutically acceptable salts."

For any structure disclosed herein, the scope of a compound also includes any tautomer which may be formed. Unless otherwise indicated, reference to a compound should be construed broadly to include pharmaceutically acceptable salts, prodrugs, tautomers, alternate solid forms, non-covalent complexes, and combinations thereof, of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counterions. Salts can form from or incorporate one or more deprotonated acidic groups (e.g. carboxylic acids), one or more protonated basic groups (e.g. amines), or both (e.g. zwitterions). Pharmaceutically acceptable salt forms include pharmaceutically acceptable acidic/anionic or basic/cationic salts. Pharmaceutically acceptable basic/cationic sate include, the sodium, potassium, calcium, magnesium, diethanolamine, romethyl-D-glneamlne, L-lysine, L-arginine, ammonium, ethanolamine, piperazine and triethanolamine salts.

Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

A prodrug is a compound which is converted to a therapeutically active compound after administration. For example, conversion may occur by the removal of a biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly depicted, a structure is intended to include every possible stereoisomer, both pure or in any possible mixture. Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

When ranges of values are disclosed, and the notation "from n1 . . . to n2" or "n1 . . . to n2" is used, where n1 and n2 are the numbers, then unless otherwise specified, this notation is intended to include the numbers themselves and the range between them. This range may be integral or continuous between and including the end values. By way of example, the range "3 to 11 membered cycloalkyl" is intended to include cycloalkyl having three, four, five, six, seven, eight, nine, ten, or eleven ring atoms. When n is set at 0 in the context of "0 carbon atoms", it is intended to indicate a bond or null.

EXAMPLES

Example 1: Inhibition of Catechol-O-Methyl Transferase (COMT)

Unless already known, the ability of a compound to act as an inhibitor of COMT is determined using a fluorescence polarization assay (Graves, T. L., et al. 2008). Compounds exhibit activity in the assay based on their ability to inhibit the production of S-adenosyl homocysteine (SAH). Any compound exhibiting an $IC_{50}$ below 1 μM is considered a COMT inhibitor. To determine $IC_{50}$ values, a 10 mM compound stock in DMSO is used to prepare a 10-point 3-fold dilution series of the compound. 1 μL of an appropriate dilution of the compound is plated into assay wells (black 96-well, round-bottom, polystyrene plates from Corning Inc., Corning, NY, Costar #3792). Recombinant enzyme is diluted in Assay Buffer (100 mM $Na_2HPO_4$ pH 7.4, 1 mM DTT, 0.005% Tween-20), and 35 μL of the diluted enzyme is added to the assay wells containing 1 μL of the diluted compound. The final amount of enzyme in the assay is varied between 1 and 6 ng depending on the preparation of COMT utilized. COMT and the compound are preincubated for about 2 h at room temperature. Enzyme reactions are initiated by the addition of 5 μL of an 8× mix prepared in Assay Buffer containing 8 μM S-adenosyl methionine (SAM) (USB Corporation, Cleveland, OH, #US10601), 16 μM dopamine (Sigma-Aldrich, St. Louis, MO, #H8502), and 40 mM $MgCl_2$. After a 25 min incubation at room temperature, reactions are quenched with 5 μL of 250 mM EDTA, pH 8.2. A 20 μL of a preformed complex containing a 1:80 000 dilution of S-adenosyl-L-cysteine (SAC) TAMRA tracer (2 mM from AnaSpec, Fremont, CA) and a 1:20 dilution of anti-S-adenosyl-L-homocysteine antibody (mouse monoclonal from IMX Homocysteine Reagent Pack, Abbott Laboratories, Abbott Park, IL, #7D29-20) was prepared in Assay Buffer B (Na2HPO4 pH 7.2). The SAH antibody/SAC TAMRA tracer complex discussed above was pre-formed at room temperature for 30 min while protected from light. Addition of 20 μl of pre-formed complex to 40 μl of the quenched reaction mix resulted in a final dilution of the SAH antibody and SAC TAMRA mix to be 1:60 and 1:240 000, respectively. After a 2.5 h incubation at room temperature, while being protected from light, fluorescence polarization was measured using a Tecan Safire2plate reader using an excitation of 530 nm and an emission of 595 nm (Tecan US, Durham, NC). Titration curves and $IC_{50}$ values were calculated using standard protocols.

Example 2: General Scheme for Making Prodrugs

Prodrugs described herein are prepared by the following general scheme.

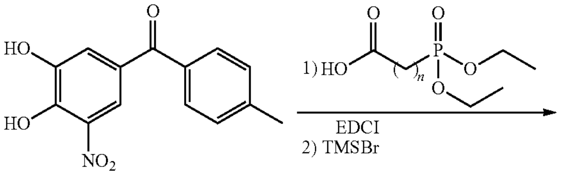

1

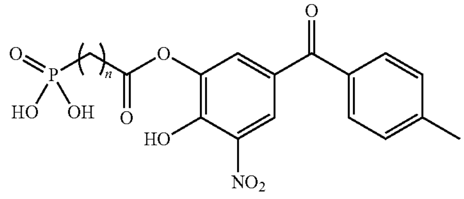

2

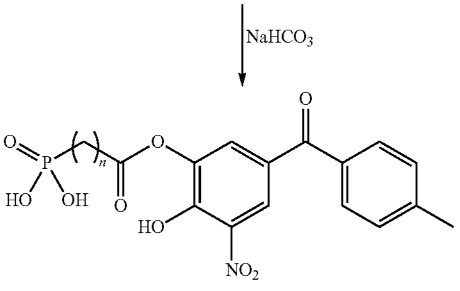

3

In the above scheme, starting compound 1 and the reagent used for reacting with the OH group are mere examples, and each may be selected as appropriate based on the desired end product. In some aspects, n is a number from 1 to 10.

Example 3: Evaluation the Efficacy of CAP4196 in Myopia Chick Model

The Myopia chick model, developed more than 35 years ago, is one of the major models for Myopia today. Major advantages of this model include: (1) relatively large eyes (8 to 14 mm), (2) rapid eye growth of about 100 μm per day, (3) highly sensitive control of refractive state by retinal image quality and focus, (4) excellent optics (diffraction-limited at 2.0 mm pupils), (5) Active accommodation (about 17 D), (6) high visual acuity (7 cycles/degree), (7) easy drug delivery by intravitreal injection, (8) Friendly and co-operative nature, and (9) inexpensive and easy to keep Three compounds, quinpirole, CAP4196, and L-DOPA (see structures below), are tested in chicks for their effects on scleral proteoglycan synthesis as a measure of scleral growth, axial elongation, and myopia.

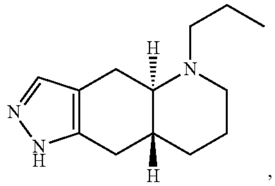

, quinpirole

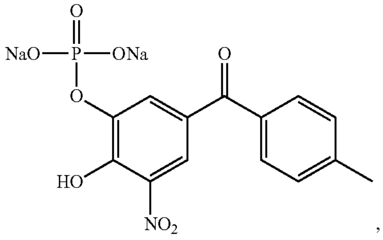

,

CAP 4196

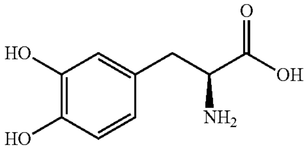

L-Dopa

Ten to thirteen chicks are tested for each of the following conditions (sample size provided in parentheses):

Group 1: Normal (n=13), Vehicle (n=13), quinpirole (n=13)

Group 2: Vehicle (n=13), CAP4196 low dose (n=13), CAP4196 high dose (n=13)

Group 3: Vehicle (n=10), L-DOPA (n=10), L-DOPA+CAP4196 low dose (n=10), L-DOPA+CAP4196 high dose (n=10).

The amount of the compound injected and the vehicle are as shown below.

Quinpirole (n=13): 10 nmoles in 20 μl injection

L-DOPA: 7.5 mM in 20 μl injection

CAP4196: low dose 0.75 mM in 20 μl injection

CAP4196: high dose 2.25 mM in 20 μl injection

Vehicle for quinpirole: Saline (20 μl, 0.75% NaCl w/v) (vehicle for quinpirole)

Vehicle for L-DOPA and CAP4196: 0.1% w/v ascorbic acid in 1× phosphate-buffered saline_(PBS)

Vehicle for L-DOPA and CAP4196: Phosphate buffered saline

Form deprivation myopia is induced in the right eyes of 4-5 days old chicks by the application of translucent occluders. Chicks receive intravitreal injections of the compound or vehicle in the form deprived eye (20 μl/eye) daily for a total of five days. Additionally, a group of normal chicks receive intravitreal injections of vehicle in their right eye, to control for changes associated with intravitreal injections ("Normal", n=13). At the end of the treatment period, chicks are sacrificed, their sclera labelled in organ culture with $^{35}SO_4$, and scleral proteoglycan synthesis measured by CPC-precipitation of newly synthesized glycosaminoglycans. Radioactivity is measured using scintillation counting, and the amount of radioactivity is compared (as CPM) between right and left eyes of all groups of animals by paired t-tests and between different groups using ANOVA. Animals are raised in the Oklahoma University Health Science Center (OUHSC) Animal facility.

Example 4: Prevention of $UVC/H_2O_2$-Induced Aggregation of Bovine Lens Extracts by CAP 1160

Figure 4:
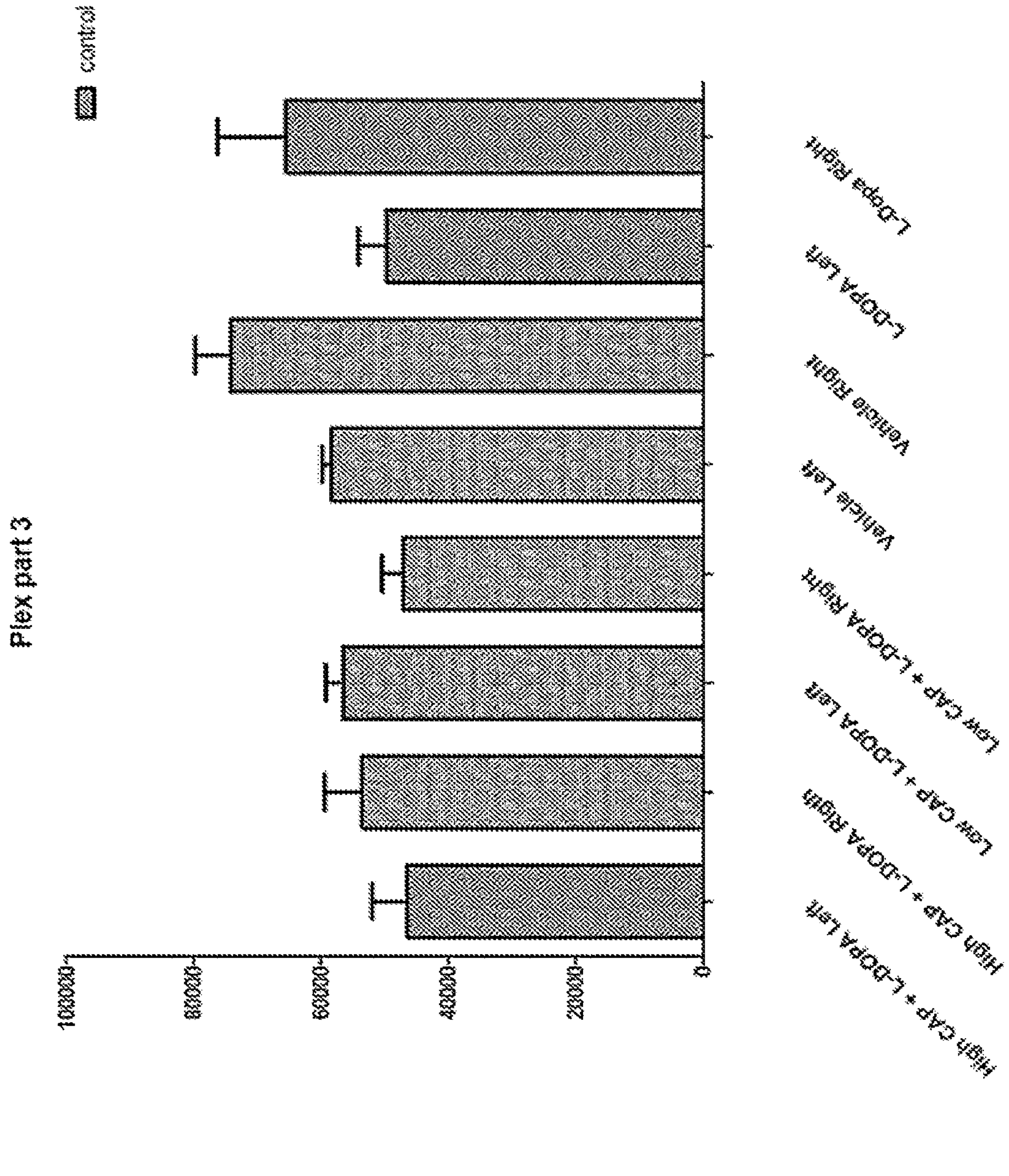

As shown in FIG. 4 (with 7 minutes exposure), CAP1160 prevents $UVC/H_2O_2$-induced aggregation of bovine lens extracts. The structure of CAP1160 is:

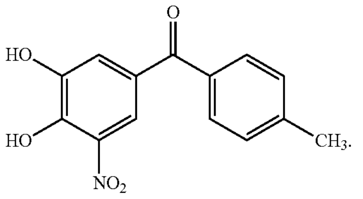 [SMILES: Cc1ccc(C(=O)c2cc(O)c(O)c([N+](=O)[O-])c2)cc1]

Example 5: Evaluation the Efficacy of CAP4719 in Myopia Check Model

Three compounds (quinpirole, CAP4719, and L-DOPA) were tested in chicks for their effects on scleral proteoglycan synthesis, as a measure of scleral growth, axial elongation and myopia. CAP4719 has the following structure:

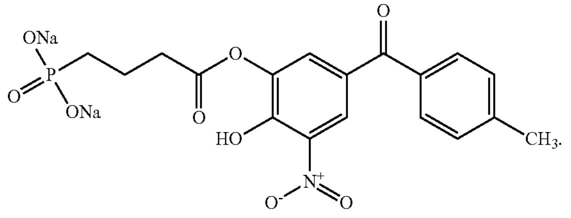

A sample size of 15 chicks for each of the following conditions (sample size in parentheses) is tested:

Group 1: Normal (n=15), Vehicle (n=15), quinpirole (n=15) [Positive control]

Group 2: Vehicle (n=15), CAP4719 low dose (n=15), CAP4719 high dose (n=15)

Group 3: Vehicle (n=15), L-DOPA (n=15), L-DOPA+CAP4719 low dose (n=L-DOPA+CAP4719 high dose (n=15).

Saline (20 μl, 0.75% NaCl w/v) (vehicle for quinpirole)

0.1% w/v ascorbic acid in 1×phosphate-buffered saline (PBS) (vehicle for L-DOPA and CAP4719)

Quinpirole (n=15), 10 nmoles in 20 ul injection

L-DOPA 7.5 mM in 20 ul injection

CAP4719 low dose 0.75 mM in 20 ul injection

CAP4719 high dose 2.25 mM in 20 ul injection

Form deprivation myopia is induced in the right eyes of 4-5 days old chicks by the application of translucent occluders. Chicks receive intravitreal injections of the compound or vehicle in the form deprived eye (20 ul/eye) daily for a total of seven days. Additionally, a group of normal chicks receive intravitreal injections of vehicle in their right eye, to control for changes associated with intravitreal injections ("Normal", n=15). At the end of the treatment period, chicks are sacrificed, their sclera labelled in organ culture with 35SO4, and scleral proteoglycan synthesis measured by CPC-precipitation of newly synthesized glycosaminoglycans. Radioactivity is measured using scintillation counting, and the amount of radioactivity compared (as CPM) between right and left eyes of all groups of animals by paired t-tests and between different groups using ANOVA. Animals are raised in an approved Animal facility and all experimental procedures will be carried out under an institutionally approved IACUC protocol.

In addition, the tissue is used for further evaluation using analytical methods to quantify levels of dopamine, metabolites (HVA & DOPAC) and CAP4719 by liquid chromatography mass spectrometry (LC/MS).

Results

Figure 3:
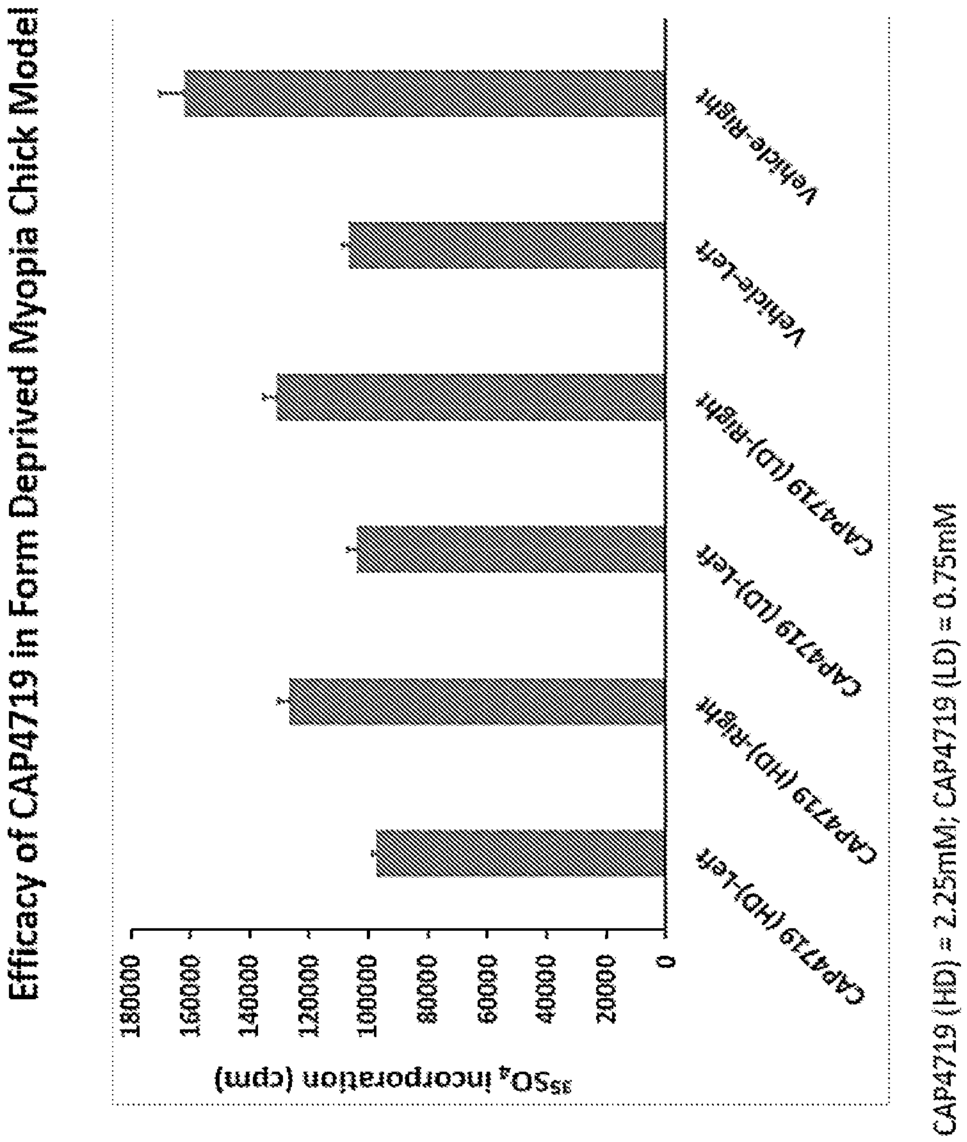
FIG. 3 and FIG. 4 represents data relating to Example 5.

The right eyes were goggled (myopic) and injected with either the high dose, low dose, or vehicle of the CAP4719 compound. Proteoglycan synthesis was measured as the amount of 35SO4 (cpm) incorporated into glycosaminoglycans four hours after the final dose. It is expected that the right eye has a higher rate of proteoglycan synthesis. The higher rate of proteoglycan synthesis is related to the increased growth rate of the myopic eye. Application of the high and low doses of the compound did not completely block the increase in proteoglycan synthesis, but the percentage increase over the left (control) eye appears to be lower in the CAP4719 treated eyes compared with the vehicle. The lower rate of proteoglycan synthesis in the right eyes of the treated eyes would be expected to cause a slower rate of elongation (and less myopia) compared with the vehicle treated eyes. Results are shown in FIG. 3 and FIG. 4.

REFERENCES

Axelrod, J., and Tomchick, R.: Enzymatic O-methylation of epinephrine and other catechols, *J Biol. Chem.* 233: 702, (1958)

Bergen, M. A. et al. Altered Refractive Development in Mice With Reduced Levels of Retinal Dopamine. *Invest Ophthalmol Vis Sci* 57, 4412-4419 (2016)

Feldkaemper, M. & Schaeffel, F. An updated view on the role of dopamine in myopia. *Exp Eye Res* 114, 106-119 (2013)

Graves, T. L., Zhang, Y., and Scott, J. E. A universal competitive fluorescence polarization activity assay for S-adenosylmethionine utilizing methyltransferases. *Anal. Biochem.* 373,296-306 (2008)

Holden, B. A. et al. Nearly 1 billion myopes at risk of myopia-related sight-threatening conditions by 2050—time to act now. *Clin Exp Optom,* 98, 491-493 (2015)

Holden B, Fricke T R, Wilson D A, Jong M, Naidoo K S, Sankaridurg P et al. Global prevalence of myopia, high myopia, and temporal trends from 2000 to 2050, Ophthalmology, 123(5):1036-42 (2016)

Iuvone, P. M., Tigges, M., Fernandes, A. & Tigges, J. Dopamine synthesis and metabolism in rhesus monkey retina: development, aging, and the effects of monocular visual deprivation. *Vis Neurosci* 2, 465-471 (1989)

Kate Thomson, Cindy Karouta, Ian Morgan, Tamsin Kelly, and Regan Ashby; Effectiveness and safety of topical levodopa in a chick model of myopia, *Sci Rep.* 9: 18345 (2019)

Mao J, Liu S, Qin W, Li F, Wu X, Tan Q; *Optom Vis Sci.* 87(1):53-60 (2010)

McCarthy, C. S., Megaw, P., Devadas, M. & Morgan, I. G. Dopaminergic agents affect the ability of brief periods of normal vision to prevent form-deprivation myopia. *Exp Eye Res* 84, 100-107 (2007)

Morgan, I. G., Ohno-Matsui, K. & Saw, S. M. Myopia. *Lancet,* 379, 1739-1748 (2012)

Morgan, I. G., He, M. & Rose, K. A. Epidemic of pathologic myopia: what can laboratory studies and epidemiology tell us? *Retina,* 37, 989-997 (2017)

Ohno-Matsui K, Yoshida T, Futagami S, Yasuzumi K, Shimada N, Kojima A. Patchy atrophy and lacquer cracks predispose to the development of choroidal neovascularization in pathological myopia. *Br J Ophthalmol,* 87:570-3 (2013)

Ohno-Matsui, K. What Is the Fundamental Nature of Pathologic Myopia? *Retina,* 37, 1043-1048 (2017)

Rein, D. B. Vision problems are a leading source of modifiable health expenditures. Invest Ophthalmol Vis Sci 54, ORSF18-22 (2013)

Tosini, G and Iuvone, P M, Role of Melatonin and Dopamine in the Regulation of Retinal Circadian Rhythms, from *The Retina and Circadian Rhythms*, Springer Series in Vision Research, Eds. Marshall, M J & Collin, S P (eds.) 2014 10.1007/978-1-4614-9613-7© Springer Science+Business Media New York 2014

Waltman S and Sears M, Catechol-O-Methyl Transferase and Monoamine Oxidase Activity in the Ocular Tissues of Albino Rabbits, *Invest Ophthalmol.,* 3:601-5 (1964)

Witkovsky, P. Dopamine and retinal function. *Doc Ophthalmol* 108, 17-40 (2004)

Wu, X. H. et al. The Role of Retinal Dopamine in C57BL/6 Mouse Refractive Development as Revealed by Intravitreal Administration of 6-Hydroxydopamine. *Invest Ophthalmol Vis Sci* 57, 5393-5404 (2016)

Other Equivalents

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed:

1. A method of treating, reducing the occurrence of, slowing the progression of, or reducing, ameliorating, or alleviating the symptoms associated with myopia, comprising administering to a subject in need thereof a compound of Formula (II), (II)

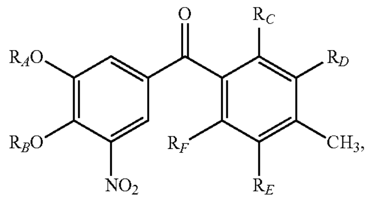

or a solvate or a pharmaceutically acceptable salt thereof, wherein, $R_A$ and $R_B$ are the same or different, and each of $R_A$ and $R_B$ is independently selected from the group consisting of: hydrogen, $R_GC{=}O$,

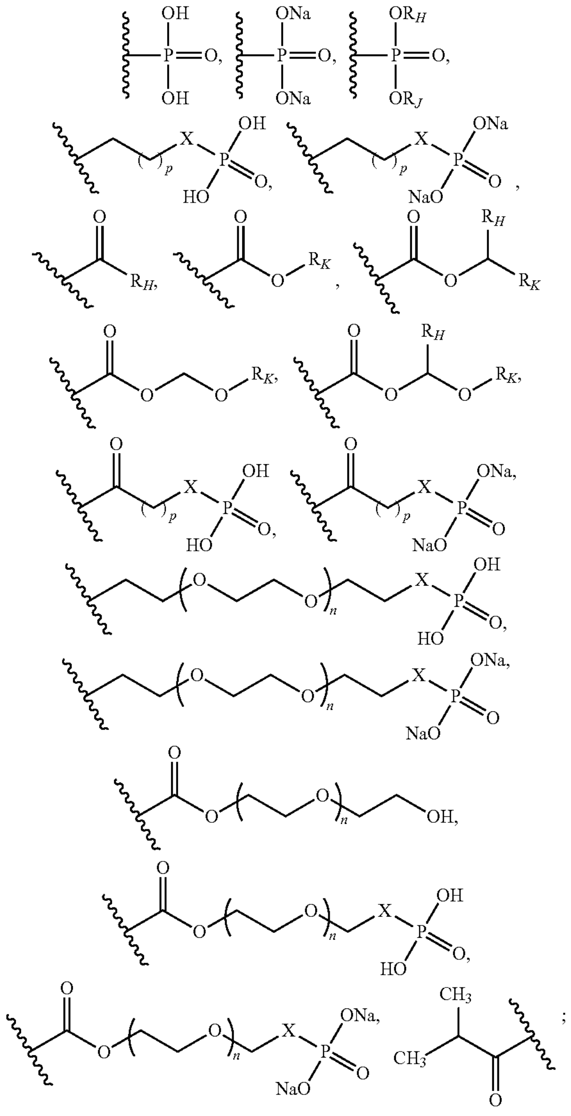

$R_C$, $R_D$, $R_E$, and $R_F$ are each the same or different, and each independently are selected from the group consisting of: hydrogen, branched or linear $(C_1\text{-}C_6)$ alkyl, halo$(C_1\text{-}C_6)$alkyl, $(C_3\text{-}C_6)$cycloalkyl, halo$(C_3\text{-}C_6)$cycloalkyl, and hydroxyl;

$R_G$ is selected from the group consisting of: branched or linear $(C_1\text{-}C_6)$alkyl; halo$(C_1\text{-}C_6)$alkyl; $(C_3\text{-}C_6)$cycloalkyl; halo$(C_3\text{-}C_6)$cycloalkyl; aryl; haloaryl; and $R_H$ and $R_J$ are each the same or different, and independently a branched or linear $(C_1\text{-}C_6)$alkyl, $R_K$ is branched or linear $(C_1\text{-}C_6)$alkyl, aryl, or

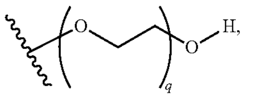

X is a C, O, or a direct bond;

n is a number from 0 to 10;

p is a number from 0 to 10; and q is a number from 1 to 10.

2. The method of claim 1, wherein $R_A$ and $R_B$ are the same or different, and each of $R_A$ and $R_B$ is independently selected from the group consisting of: hydrogen,

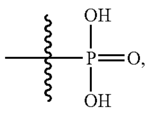
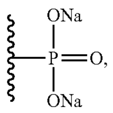
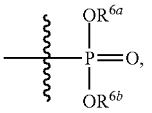

-continued

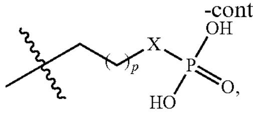
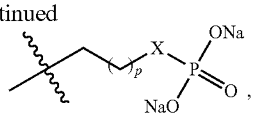

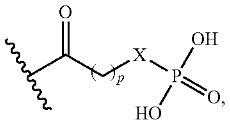
and
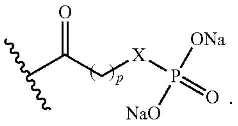

3. The method of claim 1, wherein only one of $R_A$ and $R_B$ is hydrogen.

4. The method of claim 1, wherein the myopia is high non-pathologic-myopia, pathological myopia, pseudomyopia, deprived myopia (FDM), or lens induced myopia (LIM).

5. The method of claim 1, further comprising administering an additional agent.

6. The method of claim 5, wherein the additional agent is selected from the group consisting of: COMT inhibitors, MAOI inhibitors, atropine, L-dopa, carbidopa, and non-steroidal anti-inflammatory agents.

* * * * *